(12) United States Patent
Wu et al.

(10) Patent No.: US 11,980,884 B2
(45) Date of Patent: May 14, 2024

(54) DETECTION APPARATUS FOR DETECTING ANALYTE IN A LIQUID SAMPLE AND METHOD THEREOF

(71) Applicant: Hangzhou Biotest Biotech Co., LTD., Hangzhou (CN)

(72) Inventors: Shujiang Wu, Hangzhou (CN); John Wu, San Diego, CA (US); Yangyu Zhu, San Diego, CA (US); Lorraine C. Cogan, San Diego, CA (US); Liang Hong, Hangzhou (CN)

(73) Assignee: HANGZHOU BIOTEST BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 17/539,430

(22) Filed: Dec. 1, 2021

(65) Prior Publication Data
US 2022/0088586 A1    Mar. 24, 2022

Related U.S. Application Data

(63) Continuation of application No. 15/918,030, filed on Mar. 12, 2018, now Pat. No. 11,213,814.

(30) Foreign Application Priority Data

Mar. 22, 2017    (CN) .......................... 201710172783.5
Dec. 22, 2017    (CN) .......................... 201711402474.9

(51) Int. Cl.
*B01L 3/00*    (2006.01)
*B01L 9/00*    (2006.01)
*G01N 33/94*   (2006.01)

(52) U.S. Cl.
CPC ....... *B01L 3/5023* (2013.01); *B01L 3/502723* (2013.01); *B01L 3/502746* (2013.01); *B01L 9/523* (2013.01); *G01N 33/946* (2013.01); *G01N 33/948* (2013.01); *G01N 33/9486* (2013.01); *B01L 2200/141* (2013.01); *B01L 2300/0816* (2013.01); *B01L 2300/0825* (2013.01); *B01L 2300/0851* (2013.01); *B01L 2300/0858* (2013.01); *B01L 2300/0887* (2013.01); *B01L 2300/12* (2013.01); *B01L 2300/123* (2013.01); *B01L 2400/082* (2013.01)

(58) Field of Classification Search
None
See application file for complete search history.

(56) References Cited

U.S. PATENT DOCUMENTS 7,883,899 B2 *  2/2011  Shi .................. B01L 3/5023
                                                    435/287.7

* cited by examiner

*Primary Examiner* — Jyoti Nagpaul
(74) *Attorney, Agent, or Firm* — NZ Carr Law Office

(57) ABSTRACT

The present invention discloses a detection apparatus, comprising a base layer, wherein the base layer comprises a groove for containing a testing element and a sample chamber for collecting a fluid sample. The detection apparatus can achieve fast, efficient and accurate detection of analytes in liquid samples, make operators to perform testing conveniently and freely, without causing incorrect results. In some preferred modes, the sample chamber comprises a liquid channel.

19 Claims, 13 Drawing Sheets

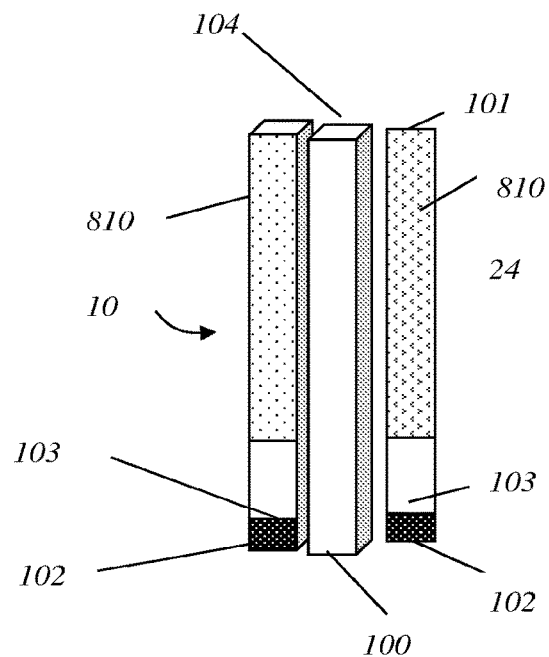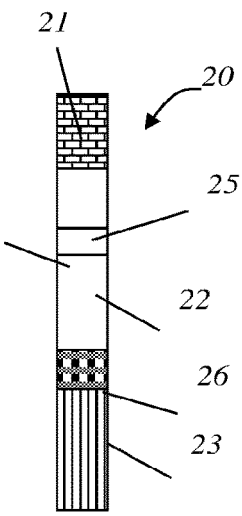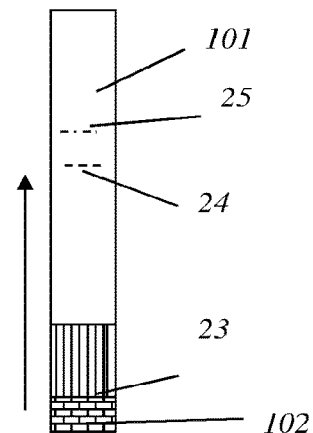
FIG.1A      FIG.1B      FIG.1C
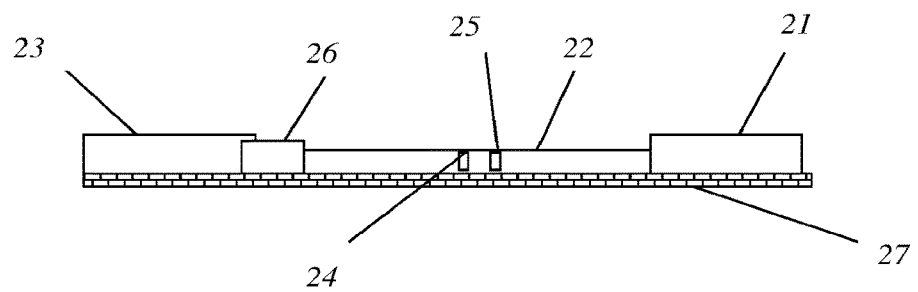
FIG.2

DETECTION APPARATUS FOR DETECTING ANALYTE IN A LIQUID SAMPLE AND METHOD THEREOF

FIELD OF THE INVENTION

The present invention relates to an apparatus for detecting analyte in a liquid sample and method thereof.

BACKGROUND

The following background art is provided to assist readers in understanding the present invention rather than a prior art.

At present, illegal drug abuse has become a recognized and increasingly worsening social problem. In 2003, the survey conducted by the US Department of Health and Human Services revealed that about 19.5 million Americans or 8.2% of people over the age of 12 are taking illegal drugs. "Recent use of illegal drugs" refers to the use of an illegal drug within one month before the US Department of Health and Human Services conducted a survey. Cannabis is found to be the most commonly used illegal drugs, accounting for 6.2% (14.6 million). Now about 2.30 million people (1.0%) are using cocaine, 604,000 people use Crack, and 1 million people are using hallucinogens, and it is estimated that 119,000 people are using heroin.

In order to fight against the drug abuse monitor this social problem, the drug testing has become a standard test procedure in various industries such as hiring, education, sports, and law enforcement, etc. To promote this effort, the drug testing industry has formed. This industry has provided a wide range of drug testing products. The urine sample collection cup for sample analysis is a classic testing product. These devices may be complex, difficult or dirty for users, or may cause the problem of adulteration in the sample to conceal the use of illegal drugs recently. In addition the urine samples cannot be collected in some cases, for example, on the roadside or in the public places.

Many other sample collection and testing devices are inefficient in extracting samples from the collection device, with many problems, such as environmental contamination caused by leakage of samples, or the test results are affected by less or more samples collected, or the detection is complicated with a number of operating steps. Many of these devices are very complex in the design and manufacturing, requiring expensive materials. Therefore, it is necessary to collect and test samples with better method and apparatus.

SUMMARY

In order to solve the problems existing in the prior art, the present invention provides a detection apparatus for detecting analyte in a fluid sample and a detection method thereof. With this apparatus and detection method, a number of problems can be avoided, so as to provide an operating method with superior performance and more reliable test results.

An object of the present invention is to provide a detection apparatus, comprising a base layer that supports testing element, wherein the base layer comprises a groove for containing a testing element and a sample chamber for collecting a fluid sample.

In some preferred modes, a testing element is provided in the groove and part of a sample applying area of the testing element is located in a sample chamber.

In some preferred modes, the apparatus further comprises a covering layer covering the groove on the base layer to form a partially sealed channel that can be used to accommodate the testing element; optionally, the covering layer covers the groove to seal. Optionally, the channel includes a testing element.

In some preferred modes, part of the sealed channels form a sample chamber to collect fluid samples. In some preferred modes, the sample chamber comprises an opening that is located at the groove, optionally, part of the groove is not sealed to form the opening, and the opening forms the sample chamber opening.

In some preferred modes, the base layer is a flat structure, on which a number of grooves that accommodate testing elements are provided.

In some preferred modes, the base layer is a rigid base layer and the covering layer is a flexible covering layer. Optionally the base layer has a certain thickness and the thickness of the covering layer is less than that of the base layer.

In some preferred modes, the base layer is transparent, the covering layer is opaque, and the opening is located on a transparent base layer; optionally, the base layer is opaque and the covering layer is transparent, and the opening is located on the covering layer; or, in both of the above means, a corresponding opening is formed on both the base layer and the covering layer as the opening of the sample chamber.

In some preferred modes, the testing element comprises a testing area and a sample applying area, wherein the testing area is at the downstream of the sample applying area.

In some preferred modes, the base layer is covered with a flexible covering layer, which makes the card slot to form a partially sealed channel. In some preferred modes, the opening is located on the base layer and this opening is used to allow the fluid sample to flow into the sample chamber. In some preferred modes, the opening is located on the covering layer and is used to allow the fluid sample to flow into the sample chamber. The fluid sample entering the sample chamber comes into contact with a portion of the sample applying area on the testing element, thereby allowing the fluid sample to flow from the testing area to the testing area, thereby completing the detection of analyte in the sample. In some preferred modes, a portion of the sample applying area of the testing element is located in the sample chamber. In some preferred modes, the seal is liquid seal or gas seal.

In some preferred modes, in a card slot that contains a testing element, the remaining portion of the card slot other than the opening for the fluid sample to flow into the sample chamber are covered by a covering layer and sealed to form a channel.

In some preferred modes, the base layer rigid structure is made by one-time molding, in particular, by one-time injection molding. The covering layer is a flexible or rigid material that can be covered on the base layer to seal the card slot so as to form an opening at one end and a sealed channel at one end, and a portion of the test strip is located in the channel. Preferably, the labeled area of the test strip and the detecting area are located in the sealed channel, wherein the opening is on a rigid base layer. In some preferred modes, the opening is located on the base layer that forms the card slot and corresponds to a portion of the sample applying area.

In some preferred modes, a structure that reduces, limits or eliminates capillary flow is located on the card slot, in particular, on the bottom surface of the card slot or the side wall of the card slot, so that liquid can flow on the testing element to the greatest extent, rather than flow along the gap formed between the test strip and the card slot. The so-called gap is the capillary gap. Said "reduces" is to allow part of the liquid not to flow through the capillary gap, said "limits" is to allow the liquid to flow through the capillary gap to the minimum, and said "eliminates" is to make no liquid to flow through the capillary gap, for example, 100% stop, 5% Stop, 90% stop, 89% stop.

In some preferred modes, a protruding tenon structure is included on the side wall of the card slot to prevent part of the liquid from flowing along the capillary gap formed by the test strip and the sidewall. For example, structures on the bottom or side wall of the card slot for reducing, limiting or eliminating capillary flow, e.g. these tenon structures can block capillary flow, and in addition, they make the gap between the test strip and the side wall of the card slot to be larger than the size of capillary flow, thereby eliminating the capillary flow of liquid through the test strip and the side wall of the card slot into the sealed card slot channel, producing a "flooding" phenomenon.

In some preferred modes, a structure that reduces capillary flow is located at the upstream of a labeled area of a testing element, or at the downstream of the testing area, or at the upstream of a sample chamber; preferably, a structure that reduces capillary flow is located at the upstream of a labeled area of a testing element, or a structure that reduces capillary flow is set corresponding to a labeled are of a testing element. In some preferred modes, the capillary flow is the capillary space formed between a test strip and a card slot, or the capillary gap formed between a test strip and the bottom of a card slot.

Of course, these tenon structures serve to fix the test strip.

In some preferred modes, the card slot comprises a pressure relief structure, or an exhaust structure, when liquid enters a sealed card slot channel by the capillary flow of test strip, the pressure in the sealed card slot channel increases. If the pressure is not released via a structure in the channel, then the capillary flow cannot continue, and the test strip does not work, forming a "non-working" phenomenon. In some preferred modes, the structure for pressure relief or exhaust is a groove structure. In a preferred mode, the groove forms a "↑" or an arrow shape. Preferably, the direction of the arrow top is consistent with the flow direction of sample on the testing element. In some preferred modes, the groove structure for pressure relief or exhaust is located at the upstream of the labeled area of the testing element, or at the downstream of the testing area or the upstream of the sample chamber; preferably, the groove structure for pressure relief or exhaust is located at the upstream of the labeled area of the testing element, or the groove structure for pressure relief or exhaust is arranged corresponding to the labeled area of the testing element. In some preferred modes, the structure for pressure relief or exhaust is located at the bottom of the card slot, wherein one end of the structure is communicated with the interior of the card slot and the other end is communicated with the outside, to facilitate the gas removal. In some preferred modes, one end of the groove structure is communicated with the interior of the card slot and the other end is communicated with the outside (for example, via an opening), to facilitate the gas removal. In some preferred modes, the structure for pressure relief or exhaust is located at the bottom of the card slot, wherein one end of the structure is communicated with the interior of the card slot and the other end is communicated with the opening, thereby facilitating the gas removal.

In some preferred modes, the sample chamber comprises a supporting structure that supports a sample applying area of a testing element so that all areas of a test strip are in a plane. In some preferred modes, the supporting structure for supporting the sample applying area is located in the sample chamber. In some preferred modes, the sample chamber is formed by or consists of a bottom, a portion of the covering layer and a portion of the base layer. Optionally, the sample chamber comprises a bottom, an opening, a portion of a covering layer, and a portion of a groove. In some preferred modes, the sample chamber has recessed side walls.

In some preferred modes, a testing element is provided in the groove and part of a sample applying area of the testing element is located in a sample chamber. Preferably, the apparatus further comprises a covering layer covering the groove on the base layer to form a partially sealed first sealed channel and a second sealed channel, the first and the second sealed channels accommodate part of the testing element and the second sealed channel forms the sample chamber. Preferably, the base layer comprises a back side and a front side, the groove is located on the back side or front side of the base layer, and the covering element covers the front side or back side of the base layer. Preferably, the detection apparatus further comprises an opening that is communicated with the sample chamber, to allow liquid to enter the sample chamber from the opening.

In some other preferred modes, the sample chamber comprises one or more liquid channels. The liquid channels are communicated with the sample applying area of the test strip. Preferably, the liquid channel is disposed at the upstream of an opening. Preferably, the liquid channel is disposed on a collection chamber. Preferably, the liquid channel is disposed at the bottom of a collection chamber. Preferably, the liquid channel exposes a portion of the test strip. Preferably, the liquid channel exposes an end portion of a test strip. Preferably, the size of the liquid channel makes the liquid sample stored in the sample chamber unable to flow out of the sample chamber through the liquid channel due to the surface tension. Preferably, the size of the liquid channel is set such that the liquid sample in the sample chamber will flow out of the sample chamber via the liquid channel that is not occupied by the test strip due to surface tension when test strip occupies a portion of the channel.

The present invention provides a method of detecting analyte in a liquid sample, the method comprising: providing a device as in any of the preceding embodiments, soaking one end of a sample chamber into the liquid sample and keeping for a period of time, then taking out and reading the test results on the testing element.

Alternatively, the present invention provides a method of detecting an analyte in a liquid sample, comprising: providing the apparatus as in any of the preceding embodiments, soaking the entire detection apparatus in a liquid sample and keeping for a period of time, then taking out and reading the result on the testing element.

In some preferred modes, "keeping for a period of time" can be 1 second to 1 hour. Preferably, keep for 1 second, 3 seconds, 5 seconds, 20 seconds, 30 seconds, 40 seconds, 50 seconds, 1 minute, 2 minutes, 3 minutes, 5 minutes, 10 minutes, 20 minutes, 30 minutes, 45 minutes, 1 hour.

In some preferred modes, the soaking is partially or entirely soaking. In some modes, including throwing, inserting or soaking the detection apparatus into the liquid sample in a random or free way for any period of time. Here, "any period of time" can be 1 second to 1 hour, e.g. 1 second, 3 seconds, 5 seconds, 20 seconds, 30 seconds, 40 seconds, 50 seconds, 1 minute, 2 minutes, 3 minutes, 5 minutes, 10 minutes, 20 minutes, 30 minutes, 45 minutes, 1 hour.

BRIEF DESCRIPTION OF THE DRAWINGS

FIG. 1 is a schematic structural diagram of a detection apparatus according to the present invention, in which FIG. 1A is a schematic diagram of a card slot on a base layer, in which the left one is a schematic diagram of a combined detection apparatus, and the middle one is a structure diagram of a base layer containing a card slot, and the right one is a structure diagram of a covering layer. FIG. 1B is a schematic structural diagram of a testing element in a specific embodiment. FIG. 1C is a schematic structural diagram of a top view of a testing element placed in a card slot.

FIG. 2 is a three-dimensional structural diagram of a testing element according to an embodiment of the present invention.

FIG. 11 is a schematic diagram of an isolated structure of a cover according to an embodiment of the present invention.

DETAILED DESCRIPTION

Figure 3:
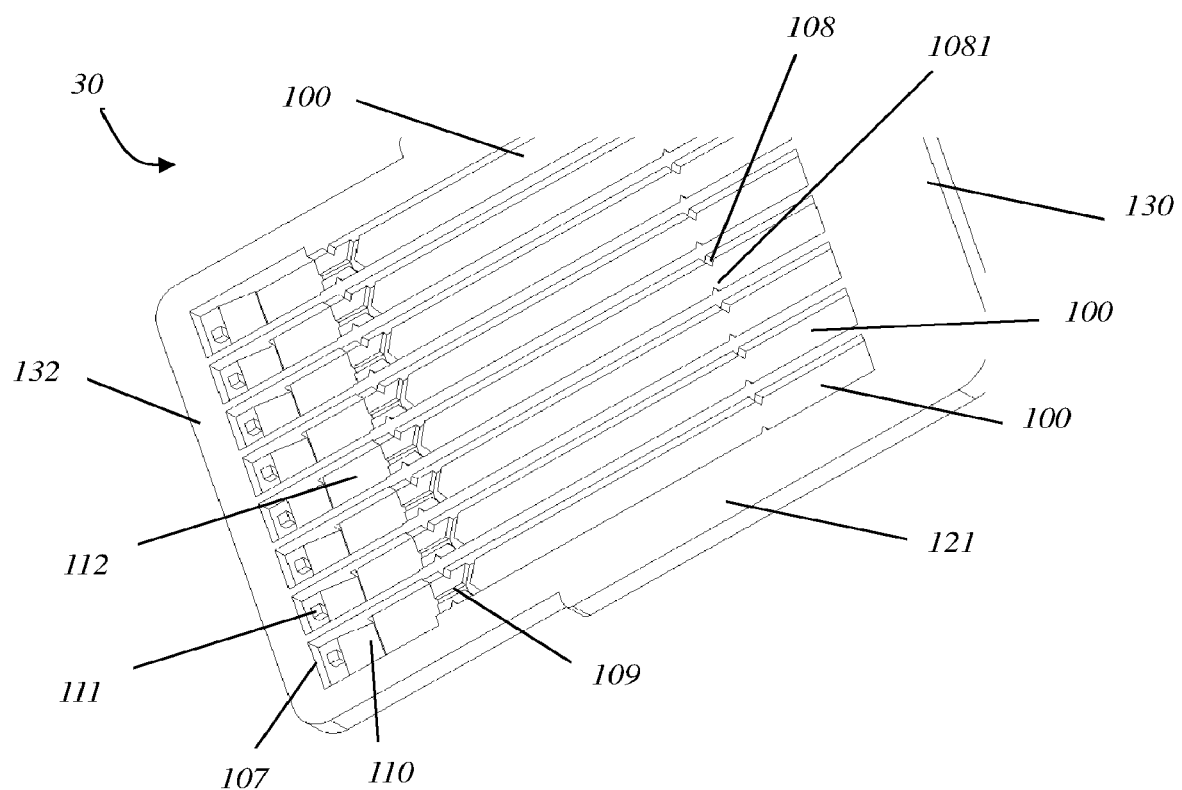
FIG. 3 is a schematic structural view (back surface) of a base layer according to an embodiment of the present invention.

The structures involved in this invention or the used technical terms are further described below. These descriptions are only to explain how to achieve the ways in this invention through examples, and will not restrict this invention.
Detection Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, and etc.
Downstream and Upstream Downstream and upstream are divided according to the flow direction of liquid, and generally, liquid flows from upstream to downstream regions. The downstream region receives liquid from the upstream region, and also, liquid can flow to the downstream region along the upstream region. Here we often divide the regions according to the flow direction of liquid. For example, on some materials that use capillary force to promote liquid to flow, liquid can flow against the gravity direction, at this time, the upstream and downstream regions are still divided according to the flow direction of liquid.
Gas Flow or Liquid Flow Gas flow or liquid flow means that liquid or gas can flow from one place to another place. The flow process may pass through some physical structures, to play a guiding role. The "passing through some physical structures" here means that passing through the surface of these physical structures or their internal space and flow to another place passively or actively, where passivity is usually caused by external forces, such as the flow of the capillary action. The flow here may mean flow of gas or liquid due to self action (gravity or pressure), or passive flow.

Testing Element

Various testing elements can be combined and applied to this invention. The testing element comprises a test strip, which can be analyzed in various forms such as immunoassay or chemical test to detect such analyte in samples as drugs or relevant metabolites indicating physical conditions. In some forms, the test strip is a water absorbent material having liquid sample adding (applying) area, reagent area and testing result area. Samples are added to the adding area, and flow to the reagent area under the capillary action. In the reagent area, samples dissolve the reagent and mix with it to detect analyte (if there is analyte in samples). Certainly, the reagent area and the sample adding area can also be the same one area. Some reagents treating liquid samples are disposed in advance in the adding area. And samples with reagents continue to flow to the testing result area. Other reagents are fixed in the testing result area, and these reagents react and combine with analyte (if there is analyte in samples) or the first type of reagent in the reagent area. In the noncompetitive detection form, if there is analyte in samples, signals will be generated; and if not, signals will not be generated. In the competitive detection form, if there is no analyte in samples, signals will be generated; and if not, signals will not be generated. The invention applies to the testing element of various analytic forms.

When the testing element is a test strip, as shown in FIG. 1C and FIG. 2, it can be made from water absorbent or non-water absorbent materials. A test strip can use various materials to transmit liquid, and one material can be superposed on another material. For example, a filter paper can be superposed on the nitrocellulose. Or in the test strip, a region that at least contains one material is located behind the other region that at least contains a different material. In such case, the liquid circulates among regions, and they can be superposed on one another or choose not to superpose. Materials on the test strip can be fixed on, for example, the holder 27 of a plastic liner or hard surface, to enhance the test strip's sustainable power. The test strip, consisting of a water-absorbing material, can flow on the test strip due to capillary action. The materials in different areas can be the same or different, and liquid flow is maintained between these areas composed of same or different materials, by this way, the sample solution can flow along the test strip.

In some embodiments where some detected objects are detected through a signal generation system (for example, at least one enzyme reacts specifically with the detected object), at least one substance generating signals can be absorbed on the analyte detecting area of the test strip, just like being absorbed specifically on the materials of the test strip as described above. In addition, substances generating signals in the sample adding area, reagent area and analyte detecting area of the test strip or all over the whole test strip can be pretreated in advance on one or more materials of the test strip, which can be achieved by adding the solution of substances generating signals to the surface of the application area or soaking one or more materials of the test strip in the signal solution, after which dry the test strip. Moreover, the above method can be used to pretreat substances generating signals in the sample adding area, reagent area and analyte detecting area of the test strip or all over the whole test strip in advance on one or more materials of the test strip. Furthermore, the signal substance existing in the sample adding area, reagent area and detecting area of the test strip can be added to one or more surfaces of the test strip materials as the labeling reagent.

Areas of the test strip 20 can be arranged as follows: a complete and necessary test strip can comprise a sample applying area 23 and a testing area 22. Generally, liquid first contacts the sample adding area, and then flows to the testing area 22 under the capillary action. Certainly, the test strip can also comprise the following areas according to the needs: a sample adding area or applying area 23, or at least a reagent area, and a testing area 22 which comprises a test result area 24, or at least a control area 25, or at least an adulteration detecting area and a liquid absorption area 21. If the detecting area comprises a control area, the preferred control area is located behind the analyte detecting area of the testing result area. All these areas or their combinations can be on a single test strip containing a material. Additionally, these areas are made from different materials, and are connected together according to the transmission direction of liquid. For example, liquid can be transmitted directly or indirectly among different areas. In this embodiment, different areas can be connected end to end or superposed mutually along the direction of liquid transmission, or connected through other materials such as connecting medium materials (water absorbent materials such as filter paper, glass fiber or nitrocellulose are preferred). By use of the connecting materials, the liquid can flow on materials that connect each area end to end, materials that connect each area end to end but the liquid does not flow, or materials that each area is overlapped mutually (including but not limited to overlapping from end to end) but the liquid does not flow.

If the test strip contains an adulteration detecting control area, the area can be arranged before or after the result detecting area. When the result detecting area contains a control area, the adulteration control area is preferred to be arranged before the control area. In one embodiment of this invention, the test strip is used for analytical judgment and/or control of adulteration. The adulteration control area can be arranged before or after the control area, and preferably, before the control area.

In the specific embodiment of this invention, any forms of testing elements or test strips can be located in a card slot or slot 100 of base layer 104, 30, or in the channel formed by covering the card slot on the base layer by the covering element. The channel formed is intended to accommodate only test strip and is not intended to be used or involved with the transmission of fluid samples. So, the fluid samples to be tested are expected to flow on the test strip by virtue of the test strip's own capillary action. However, considering the cost and testing of different analytes, usually a test strip is placed in each of multiple card slots. For example, 10 test strips can be used to test 10 different analytes. The card slots formed will affect the test results on the test strip because the card slot has physical contact with the analyte. This kind of physical contact will affect the performance of the liquid on the test strip, thereby affecting the test accuracy and effectiveness. Detailed descriptions on how to arrange the test strip in the detection apparatus and how to effectively avoid the above technical problems will be given below in the invention.

Samples

The detection apparatus provided in the invention can be used to detect samples including biological liquid (such as case liquid or clinical samples). The liquid sample or fluid sample can come from solid or semi-solid samples, including excreta, biological tissues and food samples, and these solid or semi-solid samples can be converted to liquid samples by using any suitable methods such as mixing, crushing, macerating, incubating, dissolving or digesting the solid samples in a suitable solution (such as water, phosphate solution or other buffer solutions) with the enzymolysis. "Biological samples" comprise samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is urine; food samples comprise food processed substances, final products, meat, cheese, liquor, milk and drinking water; and plant samples comprise samples from any plants, plant tissues, plant cell cutures and media. "Environmental samples" come from the environment (such as liquid samples coming from lake or other water bodies, sewage samples, soil samples, underground water, sea water and effluent samples), and can also comprise waste water or other sewage water.

Any analyte can be detected by using this invention and a suitable testing element. Preferably, this invention is used to detect the drug micromolecules in saliva and urine.

Analyte

Examples that can use the analyte related to this invention include some hapten substances, including drugs (such as drug abuse). "Drug abuse" (DOA) means to use drugs (often to paralyze the nerves) for non-medical purposes, which will lead to physical and mental damages, and people who use drugs will be dependent on, addicted to drugs and/or die. Examples of drug abuse include abuse of cocaine, amphetamine AMP (e.g. Black Beauty, white amphetamine tablets, dextroamphetamine, dextroamphetamine tablets, Beans); methylamphetamine MET (crank, meth, crystal, speed); barbiturate BAR (such as Valium, Roche Pharmaceuticals, Nutley, N.J.); sedatives (i.e. sleeping adjuvants); lysergic acid diethylamide (LSD); inhibitors (downers, goofballs, barbs, blue devils, yellow jackets, methaqualone); tricyclic antidepressants (TCA, i.e. imipramine, amitriptyline and doxepin); methylene dioxymetham-phetamine MDMA;

phencyclidine (PCP); tetrahydrocannabinol (THC, pot, dope, hash, weed and etc.); opiates (i.e. morphine MOP or opium, cocaine COC, heroin, OXY); antianxiety drugs and sedative hypnotics, the antianxiety drugs are drugs mainly used to relieve anxiety, tension, fear and stabilize emotions, having the function of hypnosis and sedation, including BZO (benzodiazepines), atypical BZ, fused dinitrogen NB23C, benzodiazepines, ligand of BZ receptors, open-loop BZ, diphenylmethane derivatives, piperazine carboxylate, piperidine carboxylate, quinazolinones, thiazines and thiazole derivatives, other heterocyclic, imidazole sedatives/painkillers (such as OXY, MTD), propanediol derivatives-carbamates, aliphatic compounds, anthracene derivatives and etc. The detection apparatus provided in this invention can also be used to detect medicines that are easy to overdose for the medical purpose, such as tricyclic antidepressants (imipramine or analogues) and acetaminophen. These medicines will be resolved into different micromolecular substances after being absorbed by human body, and these micromolecular substances will exist in blood, urine, saliva, sweat and other body fluids or in some of the body fluids.

For example, the analyte detected by this invention includes but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *staphylococcus, salmonella, fusobacterium, campylobacter, L. monocytogenes, vibrio* or *Bacillus cereus*) and substances relevant with the physiological features in the urine sample, such as pH and specific gravity. For any other clinical urine chemical analysis, the detection can be made by combining the lateral cross flow detection form and the apparatus provided in this invention.

Detection Apparatus

The detection apparatus provided in the present invention can be used to detect the presence or absence of, or the quantity of an analyte in a sample (for example, fluid sample) by using any technical principle, that is, the qualitative and quantitative detection. The detection apparatus comprises a testing element detecting the presence or absence of, or the quantity of the analyte in the sample, and also a device that accommodates the testing element.

The detection apparatus of the present invention comprises a base layer, and the base layer comprises a groove for accommodating a testing element and a covering element used for covering and sealing the groove. By this way, the covering element can cover or seal the testing element in the groove, to carry out testing of samples. Preferably, the detection apparatus further comprises a sample chamber, in which part of the sample applying area of the testing element is located in the sample chamber. Preferably, the sample chamber consists of a partial groove and a covering layer. In some preferred modes, the base layer has an opening that allows the liquid sample to enter the sample chamber. In some preferred modes, the covering layer has an opening that allows the liquid sample to enter the sample chamber.

The detection apparatus of the present invention can also be combined with other devices to complete the detection of analyte in a sample. Such devices may be a detection result reading device, a scanning device for reading the detection results, storing the result data or transmitting the data, etc. Of course, the detection apparatus of the present invention may also be disposed in some containers, such as a cup, which includes a plurality of chambers for collecting the fluid samples. The detection apparatus of the present invention is disposed in a chamber of a cup. Once the cup collects a fluid sample, the fluid sample will contact the test strip on the detection apparatus, to complete the assay.

Base Layer, Covering Element, Testing Element

The detection apparatus of the present invention comprises a base layer, and the base layer comprises one or more card slots. For example, the middle diagram in FIG. 1A in FIG. 1 shows a detection apparatus with card slot(s). The base layer 104 comprises a card slot 100. The base layer 104 has a certain thickness, and a slot (also known as card slot, channel of opening) with a certain depth can be opened in the base layer. The width of the card slot 100 is equivalent to the width for accommodating the testing element, or greater than the width of test strip, for example, for the test strip 20, card slot depth is equivalent to, or greater than the thickness of the test strip. In general, in order to save costs and miniaturize the detection apparatus, the width of the card slot is slightly larger than the width of the test strip, the depth of the card slot is slightly larger than the thickness of the test strip, and sometimes the width of the card slot is equal to or slightly less than the width of the test strip, the depth of the card slot is slightly less than or equal to the thickness of the test strip. Because the card slot is located on the base layer (the middle diagram in FIG. 1A), just covering the base layer with a covering layer 101 can seal the entire card slot and the card slot forms a sealed channel, by this way, the formed channel can accommodate testing element (the right diagram in FIG. 1A); for example, a sealed channel can accommodate a detecting area and a labeled area of a testing element. Of course, optionally, a sealed channel can accommodate a water absorption area, a labeled area and a test result area, and a test result control area of a testing element (FIG. 1C).

In general, firstly a base layer that comprises a card slot is provided. On one side of the base layer, a card slot with the length equal to the test strip is opened on one side of the base layer, and the card slot is completely exposed, and then the test strip 20 is placed in the card slot and let the test strip back side downwards (the side with a supporting structure 27), and front side upwards (the side where the detecting area or the filter paper can be seen). A covering element 101 is provided, which comprises a first covering area 810 and a second covering area 102, and an opening 103 between the first area and the second area. Finally, the covering element covers the base layer, so that the first covering area 810 covers the testing area of the testing element, and the second covering area covers a portion of the sample applying area, and let the opening 103 exposes a portion of the sample applying area. For example, in the position 102 in FIG. 1A, which is actually part of the covering element 101, part of the covering element 810 covers the card slot, forming a sealed channel at one end for accommodating part of the test strip element. The opening 103 on the covering element 101 is used to expose part of sample absorption area 23 of the testing element. Thus, one end of the card slot forms a sample chamber by a portion of the card slot on the base layer and the second covering area 102 of the covering element. The sample chamber is used to collect samples. The height of the sample chamber depends on the length of a portion of the covering element 102. The volume depends on the depth of the card slot and the height of the covering element 102. Therefore, the volume of the sample can be arbitrarily adjusted and changed by the depth of the card slot and the height of the covering element 102. Usually, once the size of the test strip and the size of the card slot is determined, the volume of the sample chamber is determined, thus playing of role of fixing the sample volume. In addition, the first covering area 810 of the covering element and part of the card slot form a sealed channel, so that the test result area and the labeled area of the testing element are located in the sealed channel. It can be said that, due to the covering element opening 103, the entire sealed card slot is divided into two sealed channels, the sealed channel (sealed in one end, non-sealed in the other end, first sealed channel) formed by the card slots covered by part of covering elements 810 is used for accommodating part of the test strip elements, for example, the test result area and the labeled area of the testing element, and this sealed channel is called the first sealed channel; and the other sealed channel (the sealed channel formed by the card slot partially covered by the covering element 102) forms sample chamber. The two sealed channels are communicated with the outside through a common opening 103, while the opening 103 is used to allow the fluid sample to enter the sample chamber. This makes it easy to collect fluid samples for quick and easy testing, as well as for freer testing. The testing can be completed without requiring much specialized knowledge and skills, thus making testing easy and user-friendly.

FIG. 1B shows a specific form of a testing element. A test strip 20 comprises a sample applying area 23 and a testing area 22. If possible, the test strip may further comprises a labeled area 26 and a sample absorption area 21, for example, testing area 22 is a nitrocellulose membrane, and sample applying area is a glass fiber. The testing area may comprise a test result area 24 and a test result control area 25. The labeled area 26 is at the downstream of the sample applying area 23 and the detecting area 22 is at the downstream of the labeled area. The detecting area comprises a test result area 24 and a test result control area. The sample absorption area is at the downstream of the test result control area.

When assembling the detection apparatus of the present invention, a card slot 100 is firstly formed on the base layer 104. The card slot can be formed by injection molding at one time, then the test strip 20 is placed in the card slot 100, allowing one end of the liquid absorption area 21 of the test strip is located at the upper part of the card slot, and the sample applying area 23 is in the vicinity of the covering element opening, corresponding to the position of the opening 103. Finally, the base layer is covered with a covering element 101, and an opening 103 is opened on the covering element so that part of the sample applying area 23 of the testing element is exposed outside through the opening 103. In addition, the end portion of the testing element at the sample applying area 23 is inside the sample chamber (the left one of FIG. 1A is an integral testing device 10, the middle one is a base layer containing a card slot, and the right one is a covering element). The top view of a complete testing device is shown in FIG. 1C, with only part of the sample applying area of partial testing element is exposed outside, and part of sample applying area is in the sample chamber. Here, the base layer can be transparent or non-transparent, while the covering layer can be partially transparent. For example, the test result area and/or the test result control area corresponding to the testing element is transparent, so as to read the result of the detecting area, while other parts can be non-transparent.

When testing is required, insert the testing device (as shown in the left diagram of FIG. 1A or the diagram of FIG. 1C) into the liquid sample, such as urine, and the liquid sample enters the sample chamber in the card slot through the opening 103. The inserted depth may just submerge the entire covering element 102 constituting the sample chamber or any height above a portion of the covering element 102 and even submerge the entire testing device in the liquid sample. This allows the liquid to easily enter the sample chamber through opening 103. When inserted into the liquid sample, the testing device can be taken out immediately or taken out after a while, then placed horizontally. The testing device can also be left in the liquid sample, by this way, as the liquid sample enters the sample chamber, the liquid contacts the sample applying area, and the liquid flows from the sample applying area 23 to the labeled area 26 along the test strip, and then flows to the testing area at the downstream, finally absorbed by the absorption area 21 (as indicated by the arrow in FIG. 1C). Due to the fact that samples are also collected or retained in the sample chamber, they are sufficient for the test strip to absorb and complete the test, which overcomes the drawbacks of the lack of liquid in the conventional art. Insufficient samples may cause unable to complete the testing; if the liquid is insufficient, it is unable to flow on the testing element, for example, unable to flow continuously when only flowing to the upstream of the test result area 24, or it is unable to wet the area due to very little liquid when flowing to the test result area 24.

The device of the present invention makes it easy, comfortable and free to operate by the testers or operators. For example, the entire testing device can also be submerged in a liquid sample, which does not allow the liquid to enter the sealed channel including the labeled area and the detecting area (herein called first sealed channel, one end is sealed, and the other is non-sealed through the opening 103 on the covering element). Because the channel at this end is sealed and the other end will be sealed by liquid flowing through the opening 103, a portion of the gas is sealed within the channel. By this way, the liquid can flow almost exclusively along the test strip from upstream to downstream based on the capillarity effect on the test strip, without additional liquid entering the channel, avoiding too much test liquid from entering the first sealed channel, thus resulting in the so-called "flooding" phenomenon that may cause inaccuracy of the test result. This make it easy and convenient for testing, so that an operator (such as a doctor or laboratory inspector) can throw the detection apparatus directly into the liquid sample and wait until the reaction is completed or the test result is available, take out the detection apparatus to read the test results.

In addition, a conventional similar detection apparatus needs to be inserted into the liquid sample for a sufficient period of time, to obtain sufficient samples. In the present invention, a sample chamber is provided at one end of the card slot and the end close to the sample absorption area of the test strip, which can be inserted into the liquid and taken out rapidly. Because adequate samples have entered the sample chamber, the testing efficiency is improved; especially when multiple samples need to be detected in a limited time, this apparatus has prominent advantages. The detection apparatus in the present invention has two sealed channels, which are communicated with the outside via the opening in the middle. The longer sealed channel accommodates the labeled area, testing area and test result control area of the test strip, and even the sample absorption area, while the shorter sealed channel accommodates part of the sample applying area, and the opening exposes a part of the sample applying area, when one end of the sample applying area is immersed into a liquid sample, such as urine, just a few seconds is enough because the sample goes into the shorter second sealed channel (forming a sample chamber) for reservation by opening during the immersion, which can continue to provide fluid sample after the liquid sample is taken out subsequently. The liquid sample flows from the upstream to the downstream of the test strip relying on the capillary flow opening of the test strip at the moment of immersion in the liquid sample, when taken out quickly, the liquid reserved in the sample chamber can continue to provide the liquid flow to complete the testing. So the operating efficiency is improved significantly. The traditional card type detection apparatus similar to the invention has no sample chamber, which will take more time to immerse the sample applying area of the test strip into the liquid sample, so the testing efficiency is not high.

In some other modes, since part of the covering element 810 covers part of the card slot, when the testing element is located in the card slot, the part of the card slot (part of the card slot covered by 810) is sealed at one end; when the detection apparatus is inserted into liquid sample, the sample does not enter the channel formed by the card slot covered by the partial covering element 810. Because one end of the channel is sealed, the incoming liquid seals a part of gas in the channel of the card slot, so that the liquid will not submerge the testing area and the labeled area no matter how long the detection apparatus is inserted in the liquid sample and how deep inserted in the liquid, thus ensuring the testing accuracy. In a more preferred mode, the labeled area and testing area on the testing element are covered and sealed by a portion of the covering element 810. More preferably, the opening 103 is located below the labeled area and retains part of the sample applying area 23. More preferably, part of the sample applying area is in the sample chamber (FIG. 1C). Unlike conventional card-type detection apparatus, the detection apparatus thus formed does not require the operator to constantly check if the card-type detection apparatus is correctly inserted in the liquid level for fear of having enough time to contact the liquid sample, nor always check if the apparatus remains vertically in the liquid. The card-type detection apparatus of the present invention can also be placed in the liquid sample at will. Even if the entire detection apparatus of the present invention is completely submerged in the liquid sample, the test result will not be affected since the liquid cannot enter the reagent area with detection functions. By providing sufficient liquid sample at the location of the sample applying area, it can guarantee the amount of liquid required for the testing. This will be further described with specific embodiments below.

The above description is to illustrate how the apparatus of the present invention is implemented using a single test strip as an example. Of course, the base layer may comprise a plurality of similar card slots. The covering element may cover and seal multiple card slot structures to form multiple openings. Each opening corresponds to a sample chamber, and each sample chamber is relatively independent, so that different analytes can be detected for the same fluid sample.

Figure 8:
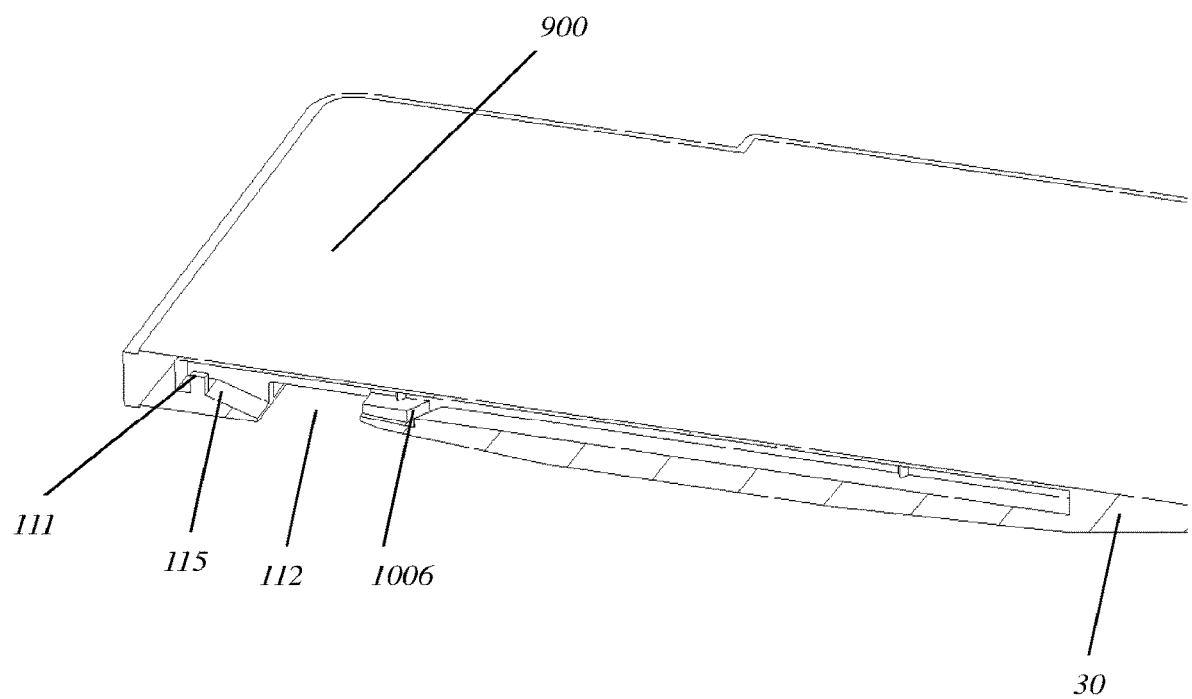
FIG. 8 is a cross-sectional structural diagram of a covering layer after covering the back of a base layer according to an embodiment of the present invention.

The base layer of the present invention can be rigid, such as plastic, aluminum alloy, etc. The covering layer can be a flexible or rigid. Optionally, the base layer and the covering layer are both rigid, and the base layer and the covering layer are bonded; or the base layer is flexible, and the covering layer is rigid. In some preferred modes, the base layer generally has a thickness, and the groove formed thereon has a suitable depth and width which is covered with a thin film layer to cover and seal the groove. In some preferred modes, the base layer has a certain thickness, the covering layer also has a certain thickness, a card slot is provided on the base layer, and a card slot is also provided on the covering layer. When the base layer and the covering layer are bonded face to face, their respective grooves correspond to form a channel. A testing element is disposed in the channel. An opening is provided either on the base layer or the covering layer, and the opening is located in the middle of the groove and at the end close to the sample applying area of the test strip. By this way, a sample chamber is formed, and the sample chamber can accommodate some samples. For example, the opening 112 is not included on the base layer, but opening 112 (FIG. 1C) is provided on the covering element, and the opening is communicated with the sample chamber, or the opening 112 is provided on the base layer but not provided on the covering element (FIG. 8); Or, the opening 112 is provided both on the base layer and the covering element at the same position, and the two openings are communicated with the sample chamber.

In some preferred modes, the base layer is rigid, with multiple card slots on the base layer, or the covering layer is transparent and flexible, or partially transparent, and in particular, the part corresponding to the testing area is transparent. In other preferred modes, the base layer is not transparent and the covering layer is transparent; alternatively, the base layer is transparent and the covering layer is not transparent. When the front of the testing element faces the base layer, the base layer can be completely transparent or partially transparent, or the base layer can be transparent corresponding to the testing area and/or labeled area on the testing element (FIG. 3). Optionally, when the front of the testing element faces the covering layer, the covering layer may be completely transparent or partially transparent, or the covering layer corresponding to the testing area and/or the labeled area on the testing element is transparent (FIG. 1C), while the base layer can be transparent or opaque.

The method of forming a card slot on the base layer can be completed by one-time injection molding or by laser etching. The rigid base layer can be made, for example, of a "thermoplastic" material, which here refers to a hot-melt plastic polymer that becomes fluid when heated and solidify into a glass substance when cold enough. This thermoplastic material can be a polymer of high molecular weight, and its links between chains rely on weak Van der Waals' force, stronger dipole-dipole interactions and hydrogen bonding or aromatic ring packing. Thermoplastic materials may include additional components, such as laser-sensitive materials. Some examples of thermoplastic materials may be acrylonitrile butadiene styrene (ABS), Poly Methyl Methacrylate-methacrylic Acid (PMMA), celluloid, cellulose acetate or cellulose acetate, Cyclic Olefin Copolymer (COC), ethylene vinyl acetate (EVA), ethylene vinyl alcohol (EVOH), fluoroplastics (PTFE with FEP, PFA, CTFE, ECTFE, ETFE), ionomers, acrylic/PVC, alloys, LCP, polyethylene (POM or acetal), polyethylene (acrylic acid), polyacrylonitrile (PAN or acrylonitrile), polyamide (PA), polyamide-imide (PAI), polyaryletherketone (PAEK or ketone), polybutadiene (PBD), polyethylene (PB), polyethylene terephthalate (PBT), polycaprolactone (PCL), polychlorotrifluoroethylene (PCTFE), polyethylene terephthalate (PET), ethylene terephthalate (PCT), polycarbonate (PC), polyhydroxy fatty acids (PHAs), Polyketide (PK), polyester, polyethylene (PE), polyetheretherketone (PEEK), polyetherketoneketone (PEKK), polyetherimide (PEI), polyethersulfone (PES), polyvinylchloride (PEC), PI, PLA, PMP, PPO, PPS, PPA, PP, polystyrene (PS), polysulfone (PSU), polytrimethylene terephthalate (PTT), polyurethane (PU), polyvinyl acetate (PVA), polyvinyl chloride (PVC), polyvinylidene chloride (PVDC) and polystyrene-acrylonitrile (SAN).

The covering elements can be polymer-formed flexible covering elements made by such materials as plastic films, double-sided tapes, polymers, etc. The element can cover a rigid base layer to seal the card slot in the rigid base layer.

It can also be made of a thin layer material formed by the above base layer material, or a thin layer flexible material formed. The concept of "rigid" and "flexible" herein is relative rather than absolute.

In some other embodiments, as shown in FIG. 3, the detection apparatus of the present invention comprises a base layer 30, and the material forming the base layer may be plastic and it is formed by injection molding at one time. One or more card slots 100 are disposed on the base layer 30, and the card slot has a certain depth and width, the width of the card slot is the same as the width of the testing element, or equal to or slightly greater than the width of the test strip. The length of the card slot is equivalent to or slight longer than the length of the test strip (FIG. 3 shows the back of the base layer). Preferably, one end of the card slot and one end close to the base layer 130 are provided with a fixing structure, for example, a pair of protruding tenon structures 108 and 1081 which are respectively disposed on the opposite side walls 1002 and 1003 (FIG. 4) that constitute the card slot. The protrusion keeps the testing element in a relatively fixed position in the card slot.

Figure 7:
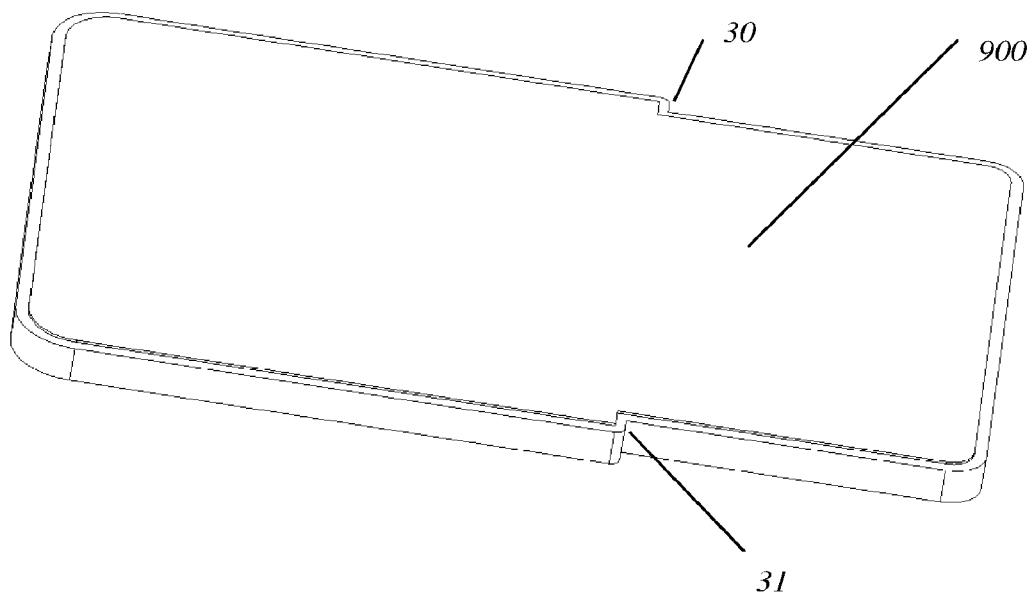
FIG. 7 is a three-dimensional structural diagram of a base layer after covering the back side (the covering layer is the back side).

There is an opening 112 at one end near the base layer 132, one opening 112 is provided at each card slot, but the opening is not disposed at the bottom end 132 of the card slot, but a certain position 902 is reserved (FIG. 7). The portion 902 reserved in the front side and the covering element subsequently covered on the card slot form a sample chamber (FIG. 8), by this way, when a multiple of card slots are formed on the base layer, a sample chamber is formed at one end 132 of each card slot, so, there is a test strip in each sample chamber or a part of sample applying area is accommodated in each sample chamber, and each test strip can be used to test different analytes. Each sample chamber forms a relatively independent space due to the side wall of the card slot. These sample chambers are independent of each other and cannot exchange liquid. In this way, the same type of liquid sample exits in the multiple sample chambers. However, since the testing elements are set for different analytes, multiple different analytes can be detected. In this way, a liquid sample can be used to test a variety of different analytes simultaneously, in addition, it avoids mutual interference between test strips with different test substances, since each sample chamber is relatively independent. Additionally, the test strip (testing area, labeled area) with the test substance is sealed within the channel, typically within the longer longitudinal channel, and a shorter sealed channel (sample chamber) is formed at the other end of the card slot in another end of the card slot, which can only accommodate part of the sample applying area, to prevent the mutual influence between different test strips.

Figure 4:
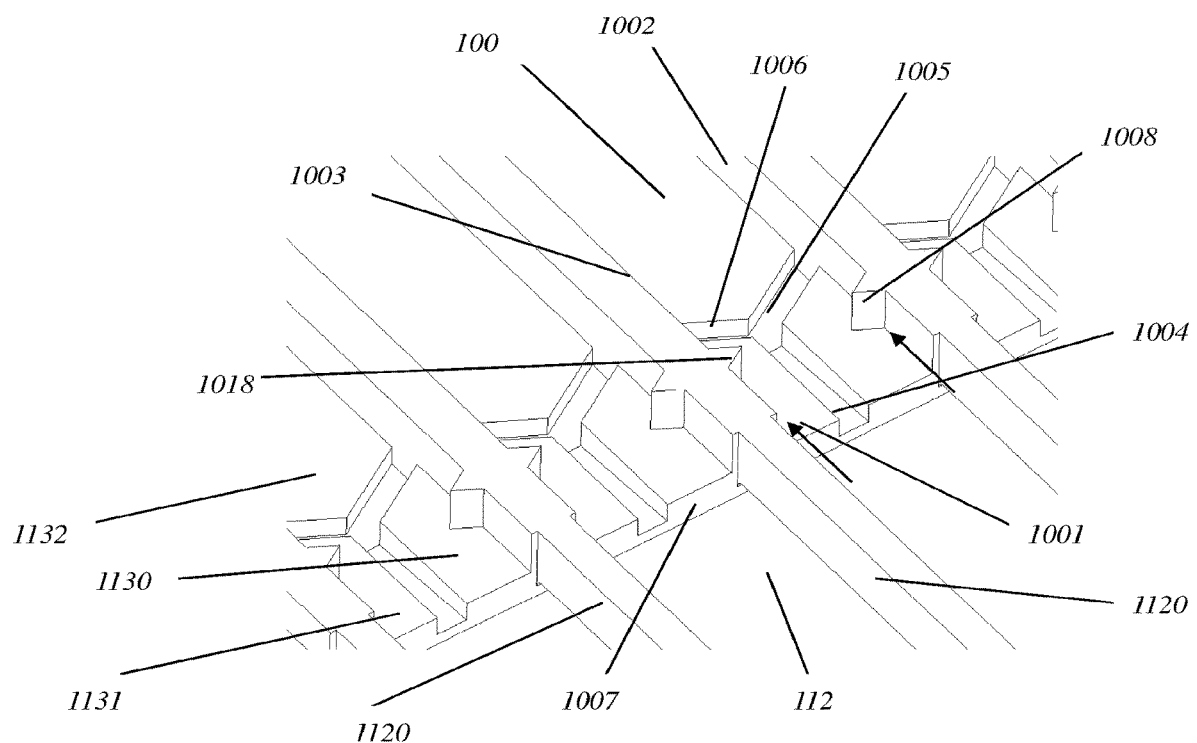
FIG. 4 is an enlarged three-dimensional structure diagram of a part of the base layer in FIG. 3.

Of course, optionally, each card slot can exist not independently at the position of opening 112, but there is no partition 1120 in the opening, forming an area without partition, which is also feasible (the partition structure as shown in FIG. 4). Of course, optionally, a sample chamber usually corresponds to a test strip. Of course, the side walls of the card slot that forms the sample chamber can also be removed. In this way, multiple test strips share a large sample chamber.

In addition, the card slot comprises a structure that reduces, prevents or limits capillary flow. In the card slot designed in this way, there are mainly two locations where the capillary gap is generated; one is the distance between the side of the test strip and the side wall of the card slot that may generate a capillary gap, thus causing capillary flow. Such capillary flow is undesirable because the resulting capillary flow causes liquid to flow to the downstream area earlier than that flowing based on capillary effect of the test strip itself, thus the liquid earlier will dissolve or wet the test strip and cause abnormal testing, called abnormal liquid samples or extra liquid samples. Because the abnormal capillary flow is only the flow of liquid samples and the normal liquid that depends on the capillarity of the test strip itself can dissolve the reagents on the test strip, such as labeling reagents, reagents for handling liquid samples, etc., the detection accuracy and sensitivity will not be affected. In general, it is required to minimize the abnormal liquid into the sealed channel and allow more normal liquid to be absorbed by the test strip, so as to make the result more accurate; on the contrary, if the entry of abnormal liquid is not controlled, the capillary action on the test strip will be affected, which eventually leads to inaccurate test results.

As shown in FIG. 4, for example, a pair of tenon structures 1008 and 1018 is also provided on the side wall of the card slot adjacent to the opening 112. The structure can play a role of fixing the test and other functional meanings. This structure can reduce, prevent or limit capillary flow. For example, the structure can protrude from the side wall, and when the width of the testing element is equal to or close to the width of the card slot, put the testing element into the card slot, and the protruding tenon squeezes the test strip, leaving a distance from the side of test strip to the side wall of the card slot. The distance is greater than the size for forming capillary, thus unable to form a capillary flow. By this way, the tenon plays a role of reducing or restricting the capillarity. In addition, even though it is possible to have a capillary gap between the test strip and the side wall of the card slot, the tenon structure is in tight compression and contact with the test strip; and the liquid from the upstream of the tenon is blocked at the tendon, so that the liquid cannot continue to flow downstream along the capillary gap, to prevent the liquid passing through the capillary gap from reaching the downstream area earlier than the liquid from the test strip, such as the labeled area or detecting area. Usually, the location of such a protruding card structure is preferably at the upstream of the labeled area or at the downstream of the sample applying area or at the upstream of the detecting area or disposed corresponding to the labeled area. Preferably, such a structure that reduces, prevents or limits capillary flow is generally disposed within a first sealed channel. This structure that reduces, prevents or limits capillary flow have another advantage when disposed at the upstream of the labeled area: in some cases, this structure will not allow more liquid to enter the first sealed channel, so that the first sealed channel is definitely sealed by the incoming liquid to form a part of closed gas in the first sealed channel, thereby ensuring independent testing of the testing element. When the liquid enters the first sealed channel through the opening, microscopically it is a gradual process, and it is always hoped that the liquid will not enter the channel any longer when entering the first sealed channel through the opening, and the tenon structure at the upstream of the labeled area acts as a barrier to prevent liquid from entering the channel, thus ensuring the sealing performance of the liquid. In this way, we need not to worry about that the liquid will enter the first sealed channel even if the apparatus in the present invention can be immersed in the liquid sample, or even free to throw into the liquid sample, which may cause abnormal liquid to enter the first sealed channel.

In some preferred modes, the structure that reduces capillary flow, for example, the tenon structure, is located at the upstream of the labeled area of the testing element, or at the downstream of the testing area, or at the upstream of the sample chamber; preferably, the groove of the structure that reduces capillary flow is located at the upstream of the labeled area of the testing element, or the structure that reduces capillary flow is disposed corresponding to the labeled area of the testing element. In some preferred modes, the capillary flow is the capillary space formed between a test strip and a card slot, or the capillary gap formed between a test strip and the bottom of a card slot. Further, a similar tenon structure may be some other structure as long as it has one or more functionally similar structures as described above. For example, the tenon structure actually protrudes upward from the surface of the side wall of the card slot, higher than the side wall plane, so that the card slot becomes narrow at the tendon. The tendon can be distributed on the surfaces of two side walls symmetrically, of course, not necessarily distributed symmetrically. In addition, there may be a number of structures that reduce, prevent or limit the capillary flow, and these structures can be distributed anywhere in the card slot, either as a single tenon structure or as multiple tenon structures that are distributed randomly rather than symmetrically. Of course, such a structure may have a recess in the side wall of the card slot, which does not enhance the stationarity of the test strip in the card slot, but increases the distance between the side of the test strip and the side wall of the card slot, and the distance is greater than the distance of capillary action. The recess may be located at the upstream of the labeled area of the test strip, which is at the downstream of the opening or at the downstream of the non-sealed end inlet of the first sealed channel.

In some preferred modes, as shown in FIG. 4, a card slot further comprises additional structure that reduces, prevents or blocks the capillary flow. The structure can minimizes the flow of liquid sample along the capillary structure (another position that may produce capillary flow) formed between the test strip and the bottom 1001 of card slot, so as to maximize the liquid sample flow along the test strip only. When the test strip is placed in the card slot, usually the front side of the test strip (the side where the testing area and the labeled area can be visually observed) is in direct contact with the bottom surface 1001 of the card slot, thus, a gap structure, such as a capillary gap structure, will be formed between the bottom surface 1001 of the card slot and the test strip. When the detection apparatus is inserted (immersed) into the liquid sample as described above, part of the liquid samples is absorbed by a portion of the sample applying area, part of them enters the sample chamber, and part of them may flow upwards by forming capillary gap between the bottom 1001 of the card slot and the front side of the test strip, causing the liquid sample to wet the labeled area or testing area earlier, while the liquid from the test strip will be delayed to reach the labeled area and testing area, thereby, resulting in inaccurate test results. When serious, it will cause the test strip not to work.

In order to avoid such problems, the card slot in the invention further comprises a structure that reduces capillary flow. The structure can reduce or prevent capillary flow of liquid outside the test strip. That is, the capillary structure allows the liquid to flow on the testing element through the capillary force of the test strip, and reduce the flow of capillary gap formed between the test strip and the card slot. In some preferred modes, as shown in FIG. 4, the structure that reduces capillary flow beyond the test strip is located on the bottom 1001 of the card slot; the structure is one or more grooves 1004, 1005 and 1006, these grooves can absorb part of liquid samples, to prevent the liquid samples from continuing to flow along the capillary gap formed by the test strip and the bottom of the card slot. There are one or more groove structures as shown in FIG. 4. The grooves form a "Y" shape, or any other shapes such as a cross or a letter shape, or round, rectangle, square, diamond, oval, etc. Of course, the groove is only one of the structures that reduce the capillary flow, and there are other structures, such as hole, cavity, trace or channel, and so on. These structures can adsorb liquid samples or prevent liquid samples from continuous flow through a large surface area, for example, once encountering the structure that reduces capillary flow, the liquid will be adsorbed or blocked, unable to or substantially unable to flow forwards or towards the downstream.

These structures that reduce capillary flow can distribute on the bottom surface 1001 of the entire card slot or can be restricted in some positions. Preferably, these structures that reduce capillary flow are located at a position of the card slot. In some modes, these structures that reduce capillary flow are located at the upstream of the test strip labeled area 26. When the liquid passes through the capillary gap formed between the bottom of card slot and the test strip and flow upwards, the liquid will be stopped or reduced at the position due to the presence of structures that reduce capillary flow, thus, the liquid samples will not wet the labeled area in advance. In some preferred modes, the structure that reduces capillary flow is located at a corresponding position in the labeled area.

In some preferred modes, the structure that reduces capillary flow is located at the downstream of the opening 112 and the upstream of the labeled area. Alternatively, the structure that reduces capillary flow is located on the bottom 1001 of the card slot near the opening.

In some preferred modes, the structural attachment that reduces capillary flow may also include another pair of structures 1018, 1008 that secure the test strip so that the card slot has a fixed structure of different locations that allows the test strip to be secured in the card slot (FIG. 4). As shown from FIG. 4 and FIG. 3, the card slot 100 has a bottom 1001 and the side walls 1002 and 1003 formed by two corresponding edges. The two edges define the depth of the card slot while the bottom 1001 defines the width of the card slot. When the card slot is formed on the base layer, the base layer has a certain thickness, so that a certain depth of groove can be easily and conveniently formed on the base layer to place the testing element with a certain thickness. In fact, the base layer for forming a card slot has two sides: one side for opening the card slot (may be referred to as the back side of the base layer) and the other side as the bottom 1001 of the card slot (may be referred to as the front side of the base layer). As the bottom surface 1001, the thickness of the card slot may be 1 mm to 8 mm, for example, for the thickness marked as 1007, it may be 1 mm to 8 mm, such as 1 mm, 2 mm, 4 mm, 5 mm, or 8 mm, etc. The thickness of the base layer can be arbitrarily chosen according to different needs. Here, the bottom 1001 of the card slot is not complete, but rather has a hollow structure at a distance. That is, the hollow forms the opening 112, but not the whole bottom 1001 of the card slot is hollow. The hollow is in the middle and two parts are reserved, one part is used to support the detection area of the test strip or to form a structure reducing capillary flow, and the other part is used to form a part of the sample chamber. The formed hollow opening 112 may be of any length, any area, any shape, e.g. rectangle, square, circle, diamond, generally the opening is used for receiving the liquid sample into the sample chamber, in addition, the opening is used for exposing part of the test strip, for example, exposing part of the sample applying area.

In addition, in order to better secure the test strip, the test strip is placed in the card slot in a balanced manner. A slightly convex area is provided at the bottom of the corresponding card slot of the tenons 1008, 1018, for example, as shown in the figure, the position of areas 1130 and 1131 is slightly higher than that of the area 1132. The two areas are higher than the area 1132 by 1 mm, 2 mm, or others.

Figure 9:
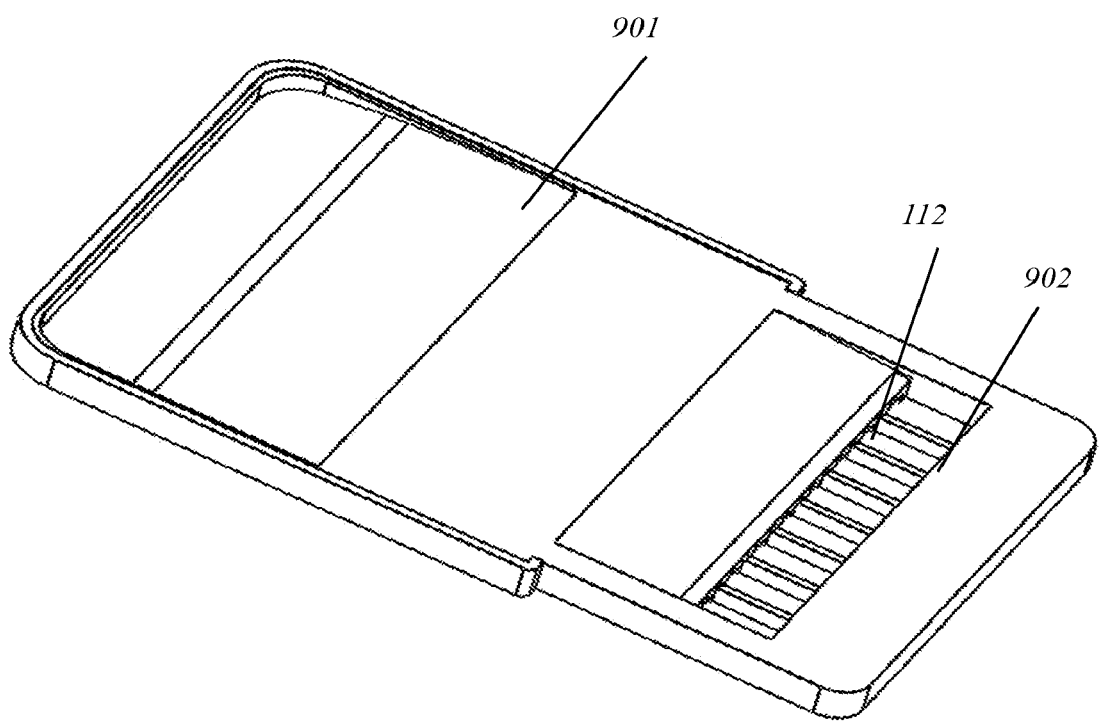
FIG. 9 is a physical structural view of the front of a base layer.
Figure 10:
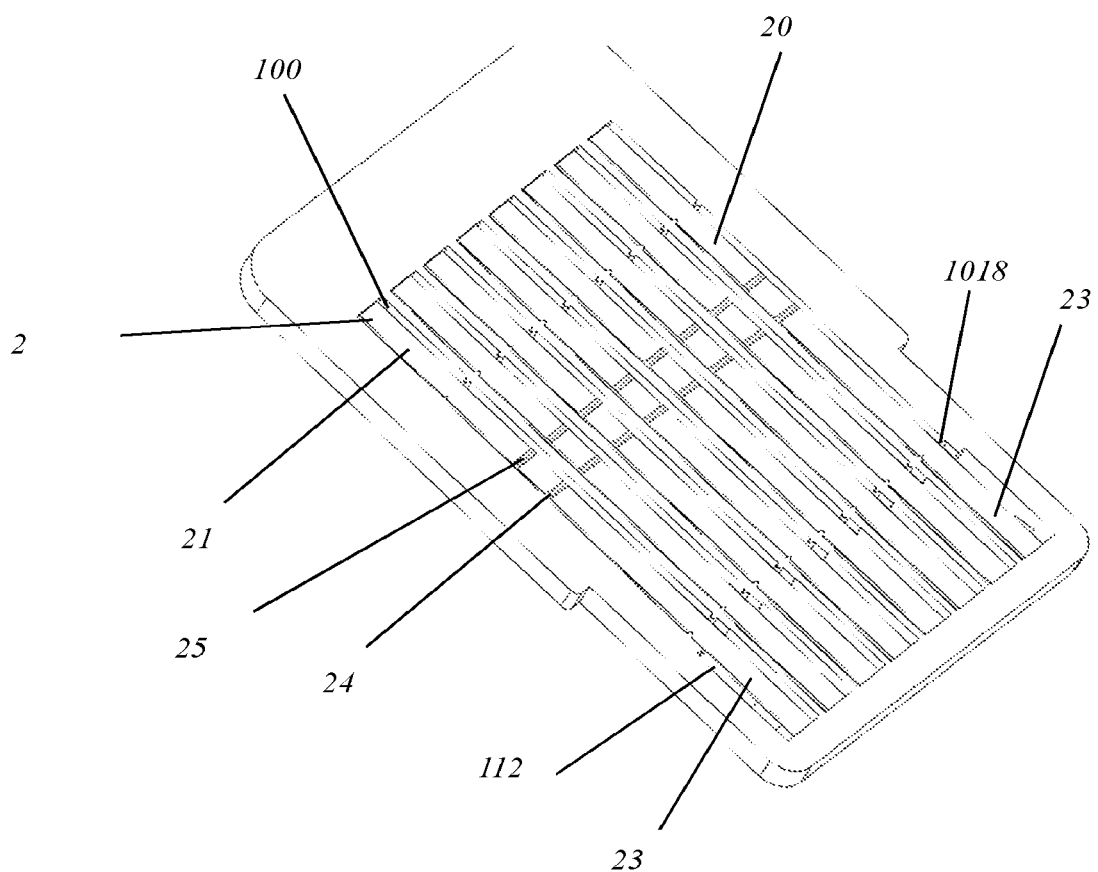
FIG. 10 is a three-dimensional structural view of a testing element placed on a base layer.

The back of the base layer is shown in FIG. 3, the front is shown in FIG. 8. When the testing element 20 is placed in the card slot, one end of the water absorption area 21 of the testing element 20 (FIG. 2) is close to the 3nd 130 of the base layer, while the end with the sample applying area 23 is close to one end of base layer 132, and the sample applying area with the absorbent material faces the front, an absorbent material of the sample absorption area such as glass fiber or other fibrous material (FIG. 1C or FIG. 10, or FIG. 2) can be seen through the opening 112. After placing the test strip, cover the back of the base layer with a flexible cover layer 900 (FIG. 8), sealing the entire card slot 100. Thus, the entire card slot at the back of the base layer is covered by the covering layer (FIG. 7). At this time, a sample chamber (second sealed channel) is formed near each end of the base layer 132 at each card slot. A portion of sample applying area 23 (FIG. 10) of the testing element is located in the sample chamber with part of the sample applying area exposed in opening 112, and the rest parts, such as the labeled area, testing area and absorption area, are covered by the covering layer and sealed to the card slot close to the other end of the base layer 130 (front side shown in FIG. 9), that is the so-called first sealed channel, both of which have entrances, in addition, the two channels are partially partitioned by the opening 112 and are also communicated with the outside. When the base layer is a transparent plastic, you can see the testing area and the labeled area through the front of the base layer. Of course, the direction of the test strip can also be the opposite to the above examples, so that the back of the test strip (the side with the supporting sheet 27) rests directly on the bottom 1001 of the card slot, leaving one side of the sample absorption area, detecting area or absorption area or labeled area is disposed facing towards the covering element. By this way, the covering element 900 covers the back of the base layer so as to seal the entire card slot, but the covering element is transparent, what is seen through the opening 112 of the base layer is the back of the support surface 27 where the sample applying area of the testing element is located, rather than the front side with the absorbent material. When testing, through the transparent covering element you can see the test results of the detecting area on the testing element. At this time, the covering element does not provide an opening 112, but only an opening 112 is provided on the base layer.

Of course, the opening element 112 can be formed simultaneously on the covering element and the base layer. The shape and size of the opening can be the same or different, so that two openings are formed to communicate with the sample chamber. When it needs to detect analyte in the liquid sample, insert the testing device consisting of the base layer, test strip and covering element into the liquid sample, insert one end with the opening 112 into the liquid sample and then take out, and allow the liquid samples to flow along the reagent strip from the sample applying area to the labeled area, then flow to the testing area, after passing through the test result area and the test result control area, and finally reach the absorption area to complete the test. Because sufficient samples are retained in the sample chamber, enough liquid can be provided to flow on the test strop and avoid the drawbacks of insufficient liquid samples in the conventional art. In addition, it is simple to manufacture such testing devices, with low cost. The base layer can be completed in one time, and the test strips are existing ones, then a covering element is covered, to complete the process. The production steps are simple and fast. In addition, as mentioned above, the detection apparatus can be completely immersed in the liquid sample to be tested directly. No matter what placing means is used, how long the time of immersion in the liquid sample, the liquid can flow normally on the test strip, to obtain the correct results. Unlike the traditional similar detection apparatus, this eliminates a lot of restrictions for operators.

In some preferred modes, the detection apparatus further comprises an exhaust, decompression or depressurization structure, one end of the structure is in gas communication with the sealed channel and the other end is in fluid communication with the outside atmosphere. The structure is used for exhausting part of the gas in the sealed channel, especially when the liquid enters the sealed channel, as a part of gas is sealed in the channel by the liquid, the pressure increases to prevent liquid from entering. In fact, in order to make the test card small and lower the cost, the width and thickness of the card slot is slightly larger than the test strip, by this way, when the test strip is in the card slot, the test strip is surrounded by the card slot, so the test strip is the channel packed by the card slot and covering layer. When the liquid enters the channel entrance (for example, the sealed channel entrance and the sample chamber opening are the same one), the liquid easily seals the channel entrance. The structure is designed to allow for the elimination of gas, allowing the liquid to enter the sealed channel to provide sufficient liquid samples. In some preferred modes, as shown in FIG. 4, the exhaust structure is located in the bottom 1001 of the card slot. There are one or more exhaust structures, and multiple grooves 1004, 1005 and 1006 are as shown in FIG. 4. The grooves form a "Y" shape, or any other shapes such as a cross or a letter shape, or round, rectangle, square, diamond, oval, etc. Of course, the groove is only one kind of the exhaust or decompression structures, and there are other structures, such as hole, cavity, trace or channel, and so on. When the liquid enters the sealed channel, one end of these grooves is in communication with the gas in the sealed channel and the other end is in communication with the gas of the outside atmosphere, so that excess gas can be removed and more liquid enters the sealed channel. Once the groove structure is sealed by liquid, the inside and outside the atmosphere of the sealed channel achieves a balance, and the liquid will no longer enter the channel. In some preferred modes, one end of the groove that is in communication with gas of the outside atmosphere is connected to opening 112, and the gas in the channel is removed through the opening.

These exhaust structures can be distributed in the entire bottom surface 1001 of the card slot, or limited to some locations. Preferably, these exhaust structures are located somewhere in the card slot. In some modes, these exhaust structures are located at the upstream of the test strip labeled area 26. In some preferred modes, the exhaust structure is located at the corresponding location of the labeled area. The exhaust structure is one or more grooves 1004, 1005, 1006, which allow the rest in the channel to be discharged to the ambient atmosphere. There are one or more groove structures, as shown in FIG. 4. The grooves form a "Y" shape, or any other shapes such as a cross or a letter shape, or round, rectangle, square, diamond, oval, etc.

Here, the exhaust groove structure and the groove that reduces capillary flow as described above can be the same structure. The structure has dual functions, one is to reduce capillary action, and the other is exhausting and reducing pressure. Of course, the two structures can be different, with their respective functions.

Figure 5:
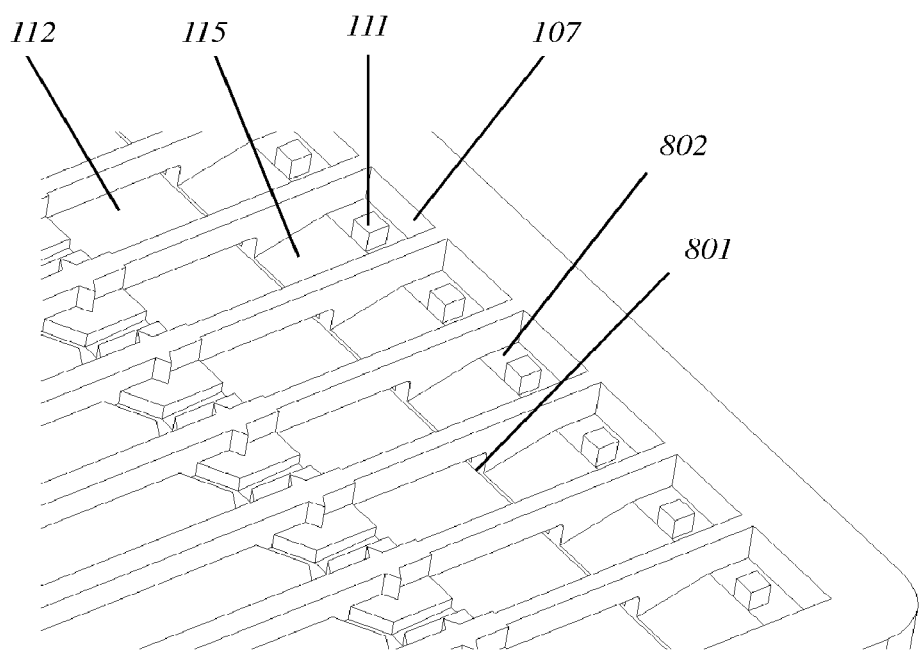
FIG. 5 is an enlarged schematic view of a partial structure of a card slot of a base layer structure according to an embodiment.
Figure 6:
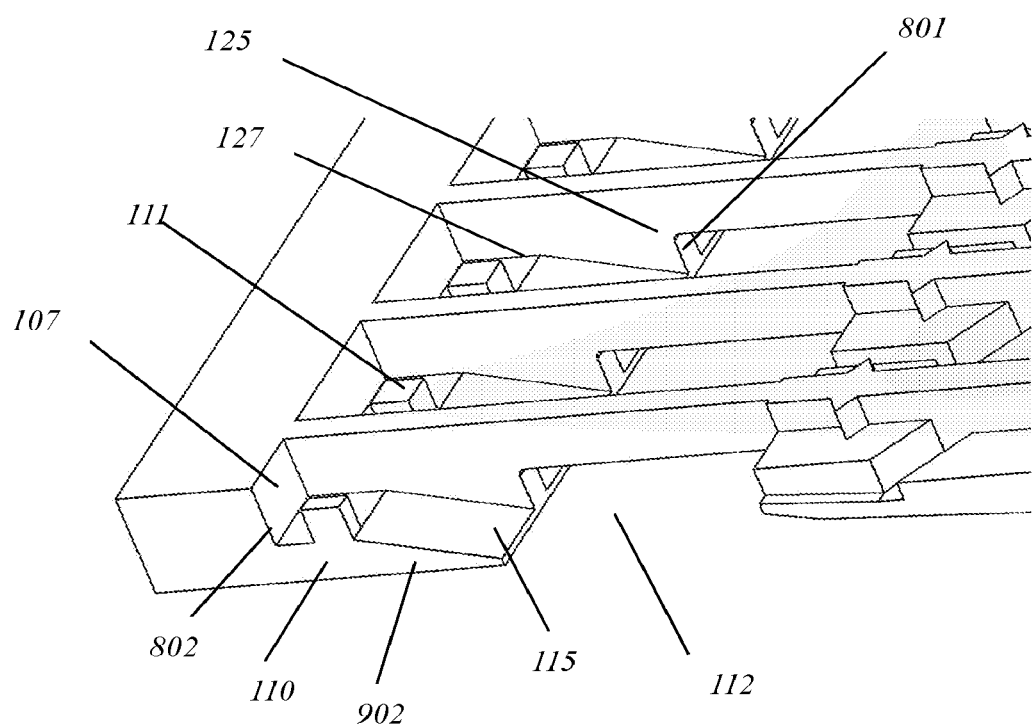
FIG. 6 is an enlarged partial schematic diagram of a card slot of a base layer structure (physical product) according to an embodiment (sample chamber position).

In some preferred modes, the sample chamber is located at one end of the base layer and near the sample applying area of the test strip. As shown in FIGS. 3, 5 and 6, the sample chamber is formed by a part of the card slot 902 on the base layer surrounded by the covering element 900. Because the base layer has a certain thickness, the card slot on the base layer has a depth, the depth of one end of the card slot close to the base layer 132 is determined by the height of the bottom 107 of the card slot. The structure area 107 constitutes the bottom area of the sample chamber, while the covering element and another area 110 at the bottom of the card slot isolated by the opening, and the two partial edges 125, 127 of the card slot form the side wall of the sample chamber, thus forming the sample chamber in the invention. The sample chamber accommodates sample applying areas of some testing elements. In some preferred modes, a protruding structure 111 is provided upwards from the bottom 802 of the card slot in the bottom area 107 close to the sample chamber. The protruding structure allows the sample applying area of the test strip close to the covering element 102, to play a role of fixing test strip. In addition, some spaces are reserved to accommodate more liquid samples. The test strip has a certain thickness, the height of the protruding structure 111 is slightly shorter than the depth of the card slot and the difference in the height is equal to the thickness of the test strip. Since the sample applying area of the test strip is usually of glass fiber with elasticity, the protruding structure 111 can press the support sheet on the back of the sample applying area of the test strip to close to the covering element. In addition, the test strip has a certain thickness, and the depth of the card slot is slightly larger than the thickness of the test strip in a certain range, usually 2-5 mm. When one end of the test strip is located in the sample chamber, it occupies the most of the volume of the sample chamber. By this way, it is difficult to allow the sample chamber to accommodate more liquid sample to wet the test strip completely, therefore, on the one hand, a protruding structure 111 can be provided to compress the soft sample applying area material, and on the other hand, it can reduce the thickness of the bottom of the card slot, for example, with a bevel 115. The bevel reduces the thickness of the bottom of the card slot, thereby increasing the volume of sample chamber. In addition, if the test strip is located too close to the bottom of the card slot (beveled position) in the sample chamber, a capillary gap will be formed, so that the liquid sample will not easily enter the sample chamber; moreover, due to the complex structure of the capillary gap, the volume of the sample chamber in a card slot is also different, increasing the inaccuracy and uncertainty of the test. Therefore, in the place close to the opening 112, the side wall of the sample chamber (for example, the bottom 1001 of the card slot) is thinned and the distance between the card slot and the test strip is increased to allow the liquid sample to enter the sample chamber. At the same time, it increases the volume of sample chamber, to provide enough liquid sample to complete the wetting of the test strip. Of course, in order to increase the sample chamber volume, the side wall (the area 110 of the base layer thickness and two opposite sides 125, 127 that form the card slot) that surrounds the sample chamber can be thinned, or depressed holes are provided on these side walls. Although these methods are feasible, it is more preferred to allow the area of the bottom 110 of the card slot to be thinner. With the above sample structure, the card-type detection apparatus is more compact, but it does not affect the superior performance of the present invention. So the cost is low but the performance is more superior.

Figure 11A:
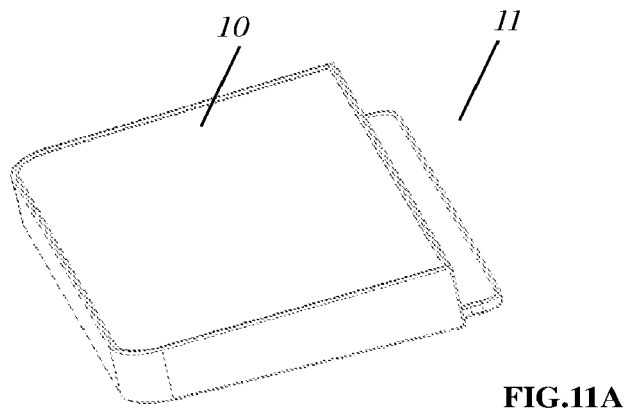
FIG. 11A is a three-dimensional structural view of a cover body.
Figure 11B:
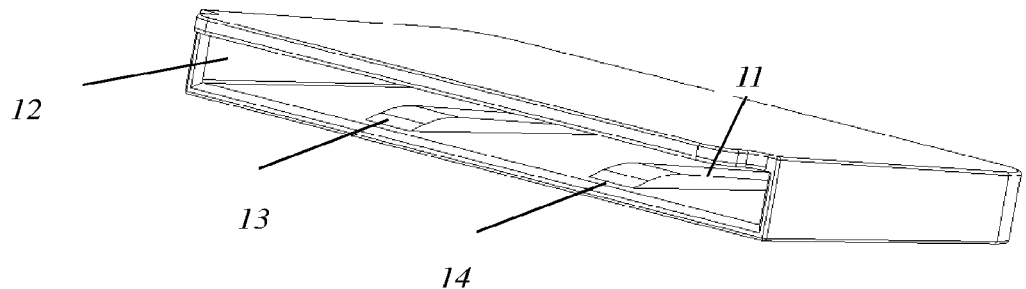
FIG. 11B is a schematic diagram of an internal structure.
Figure 11C:
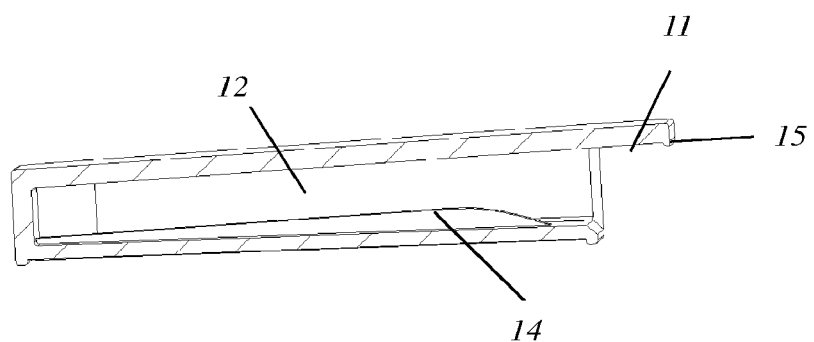
FIG. 11C is a cross-sectional structure diagram of a cover body.

In some preferred modes, a cover body component can be provided. When the detection apparatus is inserted into liquid sample, take out the detection apparatus, allow one end of the opening 112 to insert the cavity 12 of the cover body component 10, to protect the sample contact area from contamination. To limit the depth of the cover body, symmetrical limiting structures 30, 31 may be disposed on the base layer to limit the depth of the cover body insertion (FIG. 11A-B). In order to increase the stability of the cover on the base layer, two protruding fastening strips 13, 14 are provided inside the cover. When one end of the base layer is inserted into the cover body, the fastening strips 13, 14 increase the adhesion force between the cover body and the base layer, so that the cover body is not easily fallen off, thus preventing leakage of liquid sample from the opening 112 at one end of the base layer that will cause contamination of the external environment. An extended portion 11 is included at the bottom of the cover body, which is used to guide one end of the detection apparatus opening 112 to enter the cover body component 10, and prevent operators from contacting the samples. The edge of the cover body extension portion 11 also has a cover edge 15 higher than the bottom surface (higher than the plane where the extension surface is located) so that the liquid contained in the detection apparatus can be prevented from being leaked when the detection apparatus is taken out from the liquid sample, to avoid the contamination on the external environment. In some preferred modes, the fastening strips 13, 14 are arranged opposite to the extension portion so that the base layer is inserted into the cover body from a single directional position.

In another more preferred mode, if there is fewer liquid sample, the liquid sample can hardly enter the sample chamber through the opening 112 when the end of the detection apparatus with the sample chamber is inserted into the liquid sample, so that the testing element cannot be wetted. At this time, the detection apparatus must be inclined, which will increase the difficulty of operators. To better overcome such a detection apparatus, some liquid channels are provided on the sample chamber or the accessory, so that the liquid is in fluid communication with the sample applying area of the test strip. Preferably, these liquid channels are arranged at a position lower than opening 112. This allows fluid samples to be fluidly connected to the sample applying areas of test strips through these liquid channels, even though some liquid levels are lower than the opening 112.

For example, as shown in FIGS. 12-16, it is yet another more preferred embodiment of the present invention. The liquid channel 1046 is disposed at the bottom of the collection chamber with the end portion 1047 of the sample applying area 23 of the test strip exposed from the liquid channel 1046, in this way, when the end with the opening 112 is inserted into the liquid sample, the end portion 1047 of the sample applying area is brought into contact with the liquid sample. Of course, optionally, these liquid channels may not expose the sample applying area of the test strip, instead, the liquid channel is opened and the test strip does not occupy the channel space. By this way, the liquid is allowed to pass through the channel into the sample chamber to contact the sample applying area of the test strip. In some modes, the liquid channel 1046 is in rectangular shape, with the size of the channel being adapted to the size of the test strip, to substantially expose the end portion of the test strip, for example, exposed by 1-2 mm, 2-3 mm. In this way, the setting of the opening 112 and the liquid channel 1046 can satisfy more circumstances, without special limitation on the amount of liquid sample. Of course, the end portion 1047 of the test strip may not be exposed, but located inside the liquid channel. The size of the liquid channel 1046 is generally adapted to the size of the test strip. For example, it is slightly larger than the size of the test strip. The gap between the size of the liquid channel and the size of the end portion of the test strip will not allow liquid samples to drip down naturally because of the surface tension. If there is more liquid, for example, when the detection apparatus is inserted into the liquid sample, the liquid level is in the A position, the liquid sample can enter the sample chamber through the opening 112, and the liquid sample can pass through the liquid channel 1046 to contact the sample applying area of the test strip. This means that even after the liquid sample is inserted, the apparatus will be taken out in a short period of time, which firstly ensures that the liquid can be in adequately contact the liquid sample, and then the liquid sample remains in the sample chamber, to provide adequate liquid samples for the continuous flow in the test strip. The liquid channel is provided on the sample chamber, having the advantages. Usually the sample chamber has a small volume and the test strip is inserted in the sample chamber. If the liquid sample is passed through the opening 112 into the collection chamber, more space is provided to accommodate liquid samples, in addition to reduction of the thickness of the wall of collection chamber as described in the invention. But in fact, the space of sample chamber is still limited, and the liquid cannot easily fill the sample chamber quickly. Although the size of the sample chamber can be set, the size of the test strip is not always the same. This will produce a problem: each sample chamber collects different liquid sample within a period of time, so the volume of the liquid sample provided to each test strip is not the same, affecting the test results. However, when the liquid channel 1046 is disposed on the sample chamber, the liquid can fill the sample chamber (formed by the second sealed chamber) rapidly once the liquid level is higher than the opening 112. Because the air in the sample chamber can be eliminated through the liquid channel, accelerating the time and effectiveness of filling the sample chamber by liquid, basically it just takes 1 to 3 seconds to fill the sample chamber. At this time, the liquid channel 1046 can eliminate the air in the sample chamber to allow the liquid sample to quickly fill the collection chamber; in addition, it can allow the liquid sample to pass through the liquid chamber to contact the sample applying area 23 of the test strip. The requirements for the setting of channel size: when liquid samples are filled or stored in the sample chamber, the liquid samples in the sample chamber will not flow out through the liquid channel after the detection apparatus leaves the liquid samples. The liquid has a surface tension and the channel size should consider the maximum volume of liquid contained in the sample chamber. The size of the liquid channel is set to allow the liquid in the sample chamber not to flow out of the liquid channel 1046 due to surface tension. By this way, such a detection apparatus can satisfy different sample tests, in addition, it improves different applications of detection apparatus, especially when the liquid sample is very good, the setting is particularly effective.

If there are fewer liquid samples, for example, at the position of liquid level B, although the liquid samples will not enter the collection chamber through opening 112, they can pass through the liquid channel 1046 to contact the sample applying area 23 of the test strip, to complete the testing.

Usually the liquid samples enter the sample chamber from the opening 112. The liquid stored in the collection chamber is not easily leaked through the liquid channel 1046 because of the size of the liquid channel, thus ensuring the continuous flow of the subsequent liquid from the collection chamber to the test strip, to complete the entire test. Here, the shape of the liquid channel may be a rectangle as shown in FIG. 12, or a circle, a diamond, a square, an ellipse, and a combination of these shapes.

Figure 12:
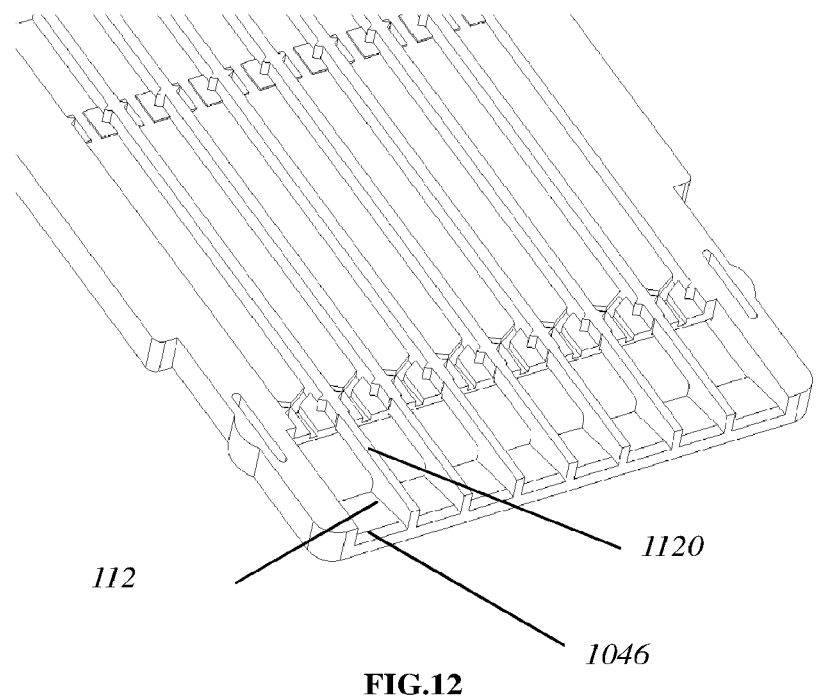
FIG. 12 is a three-dimensional structural view of a base layer according to an embodiment of the present invention (with a card slot, without a test strip).
Figure 13:
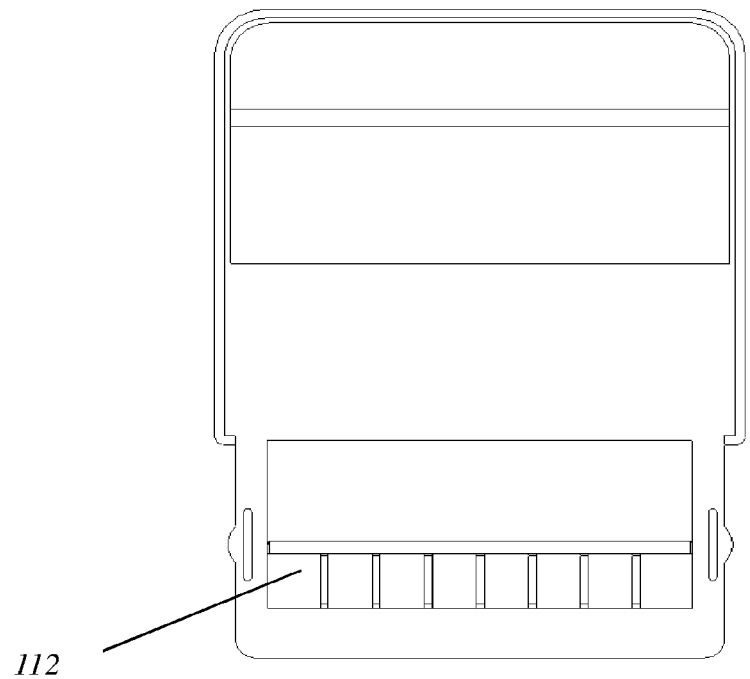
FIG. 13 is a front view of a base layer shown in FIG. 12.
Figure 14:
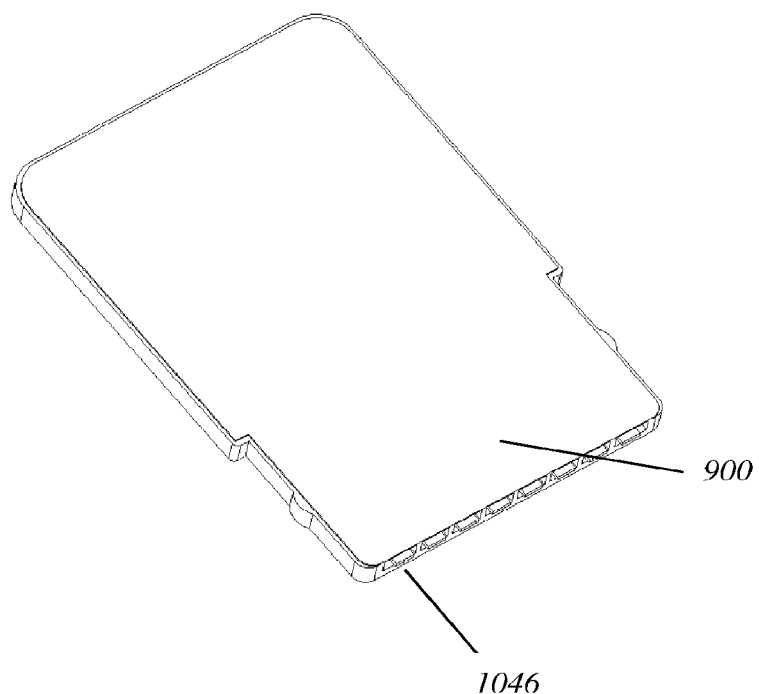
FIG. 14 is a three-dimensional structural view of a base layer as shown in FIG. 12, with a test strip provide in the card slot and a covering layer covering the test strip.
Figure 15:
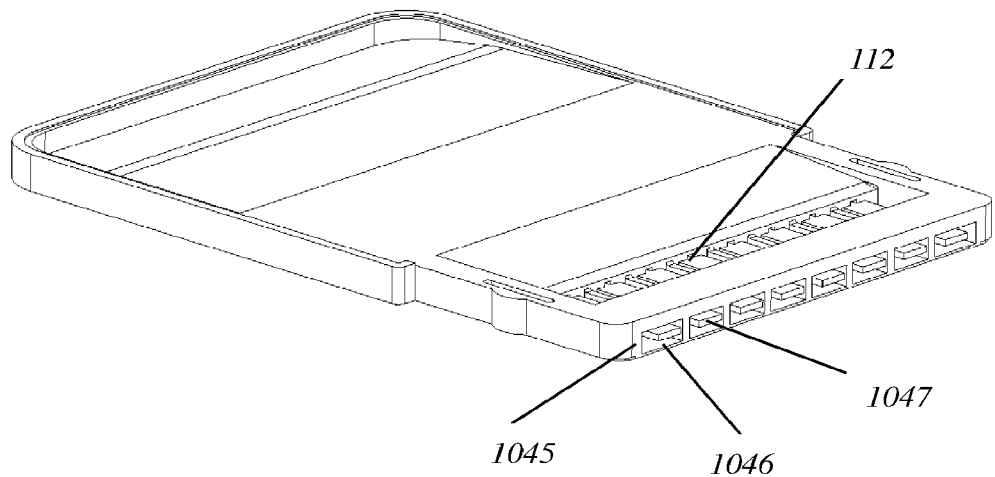
FIG. 15 is a schematic front view of a base layer of the detection apparatus shown in FIG. 14 (testing in the card slot).
Figure 16:
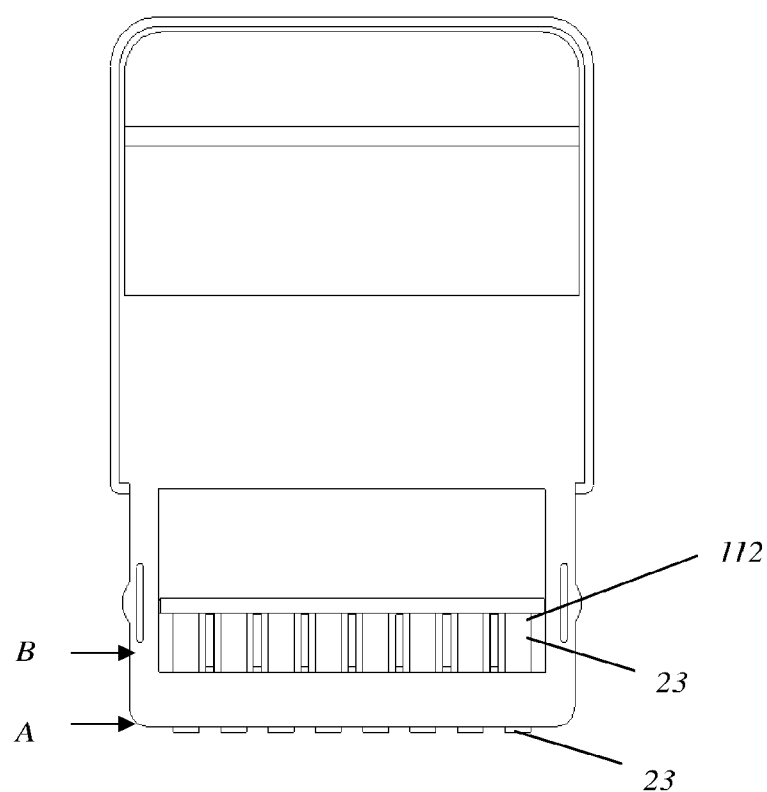
FIG. 16 is a schematic view of the use of the detection apparatus as shown in FIG. 15.

In addition to the liquid channel disposed at the bottom of the collection chamber as shown in FIG. 12, more liquid channels can be disposed at other places. The principle for setting: Some structures similar to liquid channel are disposed at the positions lower than the opening 112, to increase the opportunity of the sample applying area 23 of the test strip to contact the liquid (the liquid level is lower than the opening 112 when the liquid is less) and facilitate the operation. In addition, it can overcome some drawbacks when there is less liquid. These positions can be any position below the opening, for example, opening a channel on the wall of the sample chamber, or opening one or more liquid channels on each sample chamber. It should be noted that, these additional liquid channels designed are not essential but a preferred embodiment of the present invention.

Assembly Method of a Detection Apparatus

The present invention provides a method of manufacturing a detection apparatus which is simple and inexpensive. In some modes, a disposable injection molded base layer is provided that comprises a card slot as shown in FIG. 3 with a certain depth and width. The width of the card slot is equivalent to the width of the accommodated testing element, which can be equal to or slightly greater than the width of the test strip; the length of the card slot is equivalent to or slightly longer than the length of the test strip (FIG. 3 shows the back view of the base layer and the FIG. 8 shows the front view of the base layer). Preferably, one end of the card slot and one end close to the base layer 130 are provided with a fixing structure, for example, a pair of protruding structures 108 and 1081. An opening 112 is provided at the end close to the base layer 132, and an opening 112 for each card slot. But the opening is not provided at the bottom end 132 of the card slot, but a certain position 102 is reserved (FIG. 5), as the previously described hollow opening 112. A testing element is provided, comprising a sample applying area, a labeled area, a testing area, and a water absorption area. The sample applying area is located at the upstream of the labeled area. The testing area is located at the downstream of the labeled area. The testing area comprises a test result area and a test result control area (FIG. 1B and FIG. 2). The test strip is placed in the card slot so that one end of the sample applying area corresponds to opening 112 of the card slot, and the one end of the absorbent area is near the end of the base layer 130; in addition, a portion of the sample applying area is inside the sample chamber and relies on the protruding structure 111 inside the sample chamber. Additionally, the labeled area of the reagent strip is located at the upstream of the structures that reduces the capillary flow, while leaving the side of the test strip with support sheet 27 exposed through the card slot. A flexible covering layer is provided that covers the back of the base layer to seal the entire card slot while bonding the surface of the test with the supporting sheet 27; at the same time, the covering element such as double-sided tape, bonding films, etc., and the portion 902 of the front side of the card slot forms a sample chamber, exposing a portion of the sample applying area through opening 112, and the labeled area and testing area are sealed in the card slot (first sealed channel) by the covering layer. Of course, the base layer may comprise a plurality of similar card slot structures. The covering element is adapted to the size of the back of the base layer, and only one covering element is required to seal multiple card slots (forming a plurality of similar first and second sealed channels). Thus, testing elements are placed in each card slot for testing different analytes, to form a sample chamber in each card slot. Multiple different analytes can be detected simultaneously for the same sample.

Detection Method

In another aspect, the present invention provides a method of detecting analyte in a liquid sample, comprising: inserting the detection apparatus in any of the foregoing modes into a liquid sample and soaking at will to liquid sample, then taking out and reading the test results on the testing area through the front of a transparent base layer or a covering element. It can be read by naked eyes or by a machine, for example, quantitative reading by the machine designed according to the optoelectronic principle or scanning to save the test results through a scanner. The time from insertion, soaking at will to the liquid sample can be 1 second, 2 seconds, 3 seconds, 4 seconds, 5 seconds, 6 seconds, 7 seconds, 8 seconds, 10 seconds, 12 seconds, 15 seconds. After taken out, assay or testing can be carried out by a test strip.

Inserting herein means that, firstly contacting the end with sample chamber with liquid samples, then taking out, or firstly contacting the end with sample chamber with samples, then continuously inserting to allow the whole detection apparatus to be immersed in the liquid sample.

Example 1

Referring to FIGS. 2-8, a detection apparatus of the present invention is provided with a plastic rigid base layer structure. Eight card slots with the same structure are provided on the rigid base layer as shown in FIG. 2. Each test strip can be used to detect analytes such as amphetamine, cocaine, methamphetamine, opiates, THC and phencyclidine in urine, respectively. Using gold particles as a labeling material, these analytes are detected by the competitive methods. The front side of the test strip is mounted to a card slot in the direction of opening 112, and the absorbent material on the sample applying area of the test strip can be seen from the opening 112, such as glass fiber, and then transparent adhesives with the same size as the base layer are covered on the back of the base layer, thus forming a detection apparatus.

Fifty negative samples are mixed with mixtures of drug abuse, including amphetamines, cocaine, methamphetamine, opiates, THC and phenylcyclohexane, in addition, 50 negative samples are provided.

When testing, insert the detection apparatus (detection card) into these urine samples and immerse them in the urine for 30 seconds, 1 minute, 2 minutes, 3 minutes, 5 minutes, or let the entire detection apparatus freely throw into the liquid sample for soaking for more than 1-15 minutes, to detect by the detection apparatus. Eventually, the flow of liquid can be completed correctly to get effective results, indicating that the apparatus is more casual and user-friendly while ensuring the accuracy of the results.

Example 2

In contrast to Example 1, a detection apparatus as shown in FIGS. 12-16 is provided, with a liquid channel 1046 on the bottom of each sample chamber. The size of the test strip is 2 mm thick and 6 mm wide. The volume of the sample chamber (without the test strip) is 2 ml. The length and width of the liquid channel are mm, respectively.

Fifty negative samples are mixed with mixtures of drug abuse, including amphetamines, cocaine, methamphetamine, opiates, THC and phenylcyclohexane, in addition, 50 negative samples are provided.

When testing, insert the detection apparatus (detection card) into these urine samples and immerse them in the urine for 1 second, 3 seconds, 5 seconds, 7 seconds, 9 seconds, 1 minute, 2 minutes, 3 minutes, 5 minutes, or let the entire detection apparatus freely throw into the liquid sample for soaking for more than 15 minutes, to detect by the detection apparatus. Eventually, the flow of liquid can be completed correctly to get effective results, indicating that the apparatus is more casual and user-friendly while ensuring the accuracy of the results.

The invention shown and described herein may be implemented in the absence of any elements, limitations specifically disclosed herein. The terms and expressions used herein are for illustration rather than limitation, which do not exclude any equivalents of the features and portions described herein in the use of these terms and expressions, in addition, it should be understood that various modifications are feasible within the scope of the present invention. It is therefore to be understood that, although the invention has been particularly disclosed by various embodiments and alternative features, modifications and variations of the concepts described herein may be employed by those of skilled in the art, and such modifications and variations will fall into the scope of protection of the present invention as defined by the appended claims.

The contents of the articles, patents, patent applications, and all other documents and electronic information available or documented herein are incorporated herein by reference in their entirety, as if each individual publication is specifically and individually indicated for reference. The applicant reserves the right to incorporate any and all materials and information from any such article, patent, patent application or other document into this application.

What is claimed is:

1. A detection apparatus for detecting an analyte in a liquid sample, comprising:
   a groove configured to contain a test strip therein, the test strip comprising a sample applying area and a test area;
   a sample chamber, wherein a part of the sample applying area is located in the sample chamber;
   a covering layer covering the groove to form a first sealed channel and a second channel, the first sealed channel accommodating the test area of the test strip and the second channel forming the sample chamber, wherein the sample chamber is configured to retain an amount of the liquid sample sufficient for the sample applying area of the test strip to absorb the amount of the liquid sample; and
   an opening in fluid communication with the sample chamber, wherein the opening is configured to allow the amount of the liquid sample to enter into the sample chamber for contacting the sample applying area when an end of the detection apparatus with the opening is inserted into the liquid sample, and the opening corresponds to the sample applying area on the test strip, and the opening exposes a portion of the sample applying area, and
   one or more liquid channels, and the liquid channels are in fluid communication with the sample chamber.

2. The detection apparatus according to claim 1, wherein the one or more liquid channels are disposed upstream of the opening.

3. The detection apparatus according to claim 1, wherein the one or more liquid channels are disposed on the sample chamber as to eliminate the air in the sample chamber.

4. The detection apparatus according to claim 1, wherein the one or more liquid channels are disposed at the bottom of the sample chamber.

5. The detection apparatus according to claim 1, wherein a portion of the test strip is exposed through the one or more liquid channels.

6. The detection apparatus according to claim 1, wherein an end portion of a sample applying area of the test strip is exposed through the one or more liquid channels.

7. The detection apparatus according to claim 6, wherein a gap existing between a wall of the one or more liquid channels and the end portion of the test strip prevents liquid samples to drip down.

8. The detection apparatus according to claim 1, wherein the size of the one or more liquid channels makes the liquid sample stored in the sample chamber unable to flow out of the sample chamber through the one or more liquid channels due to the surface tension.

9. The detection apparatus according to claim 1, wherein the detection apparatus further comprises a base layer comprising a back side and a front side, the groove is located on the back side or front side of the base layer, and the covering layer covers the front side or back side of the base layer.

10. The detection apparatus according to claim 9, wherein the base layer is a rigid base layer and the covering layer is a flexible or rigid covering layer.

11. The detection apparatus according to claim 1, wherein the opening is formed from hollow adjacent areas at the bottom of the groove.

12. The detection apparatus according to claim 1, wherein the detection apparatus further comprises a structure that reduces, limits or eliminates capillary flow and prevents liquid from flowing through a capillary gap formed between the test strip and a side wall of a card slot.

13. The detection apparatus according to claim 1, wherein the liquid sample is urine.

14. A method for detecting an analyte in a liquid sample, comprising:
providing a detection apparatus comprising:
a groove configured to contain a test strip therein, the test strip comprising a sample applying area and a test area;
a sample chamber, wherein a part of the sample applying area is located in the sample chamber;
a covering layer covering the groove to form a first sealed channel and a second channel, the first sealed channel accommodating the test area of the test strip and the second channel forming the sample chamber; and
an opening being in fluid communication with the sample chamber, wherein the opening corresponds to the sample applying area on the test strip, and the opening exposes a portion of the sample applying area; and
inserting an end of the detection apparatus with the opening into the liquid sample for a period of time as to making the liquid sample flow into the sample chamber through the opening.

15. The method according to claim 14, wherein the period of the time is from 1 second to 50 seconds.

16. The method according to claim 15, wherein the period of the time is from 1 second to 15 seconds.

17. The method according to claim 14, further comprising after the period of the time, picking up the detection apparatus out of the liquid sample.

18. The method according to claim 14, wherein the detection apparatus further comprises one or more liquid channels, and the one or more liquid channels are in fluid communication with the sample chamber; and wherein when inserting the end of the detection apparatus with the opening into the liquid sample for a period of time as to making the liquid sample flowing into the sample chamber through the liquid channels.

19. The method according to claim 14, the liquid sample is urine.

* * * * *